United States Patent
Burton et al.

(10) Patent No.: US 7,132,458 B2
(45) Date of Patent: Nov. 7, 2006

(54) OXIDIZED CAROTENOID FRACTIONS AND KETOALDEHYDE USEFUL AS CELL-DIFFERENTIATION INDUCERS, CYTOSTATIC AGENTS, AND ANTI-TUMOR AGENTS

(75) Inventors: Graham Burton, Ottawa (CA); Janusz Daroszewski, Ottawa (CA); Jenny Phipps, Chelsea (CA); Prabhat Arya, Orleans (CA)

(73) Assignee: Chemaphor Inc., Ontario (CA)

( * ) Notice: Subject to any disclaimer, the term of this patent is extended or adjusted under 35 U.S.C. 154(b) by 0 days.

(21) Appl. No.: 10/196,695

(22) Filed: Jul. 15, 2002

(65) Prior Publication Data

US 2003/0096875 A1    May 22, 2003

Related U.S. Application Data

(60) Continuation-in-part of application No. 09/651,250, filed on Aug. 30, 2000, now abandoned, which is a division of application No. 08/527,039, filed on Sep. 12, 1995, now abandoned, which is a continuation-in-part of application No. 08/288,315, filed on Aug. 10, 1994, now Pat. No. 5,475,006.

(51) Int. Cl.
| | |
|---|---|
| *A01N 35/00* | (2006.01) |
| *A01N 31/04* | (2006.01) |
| *A61K 31/12* | (2006.01) |
| *A61K 31/11* | (2006.01) |
| *A61K 31/07* | (2006.01) |

(52) U.S. Cl. .................. 514/675; 514/690; 514/693; 514/703; 514/725

(58) Field of Classification Search ................ 514/690, 514/703, 675, 693, 725
See application file for complete search history.

(56) References Cited

U.S. PATENT DOCUMENTS

| | | |
|---|---|---|
| 4,105,855 A | 8/1978 | Schulz et al. |
| 4,127,455 A | 11/1978 | Schulz et al. |
| 4,351,346 A | 9/1982 | Brummer et al. |
| 4,996,069 A | 2/1991 | de Hay et al. |
| 5,084,292 A | 1/1992 | Van Dort et al. |
| 5,097,063 A | 3/1992 | Moldt |
| 5,225,604 A | 7/1993 | Moldt |
| 5,310,554 A | 5/1994 | Haigh |
| 5,358,915 A | 10/1994 | Nebergall et al. |
| 5,475,006 A | 12/1995 | Burton et al. |

FOREIGN PATENT DOCUMENTS

| | | |
|---|---|---|
| WO | WO96/05160 | 2/1996 |

OTHER PUBLICATIONS

"Remington: The Science and Practice of Pharmacy" (20th ed.), A.R. Gennaro, 2000, p. 858-861,963.*
Hardman et al. "Goodman & Gilman's The Pharmacological Basis of Therapeutics" (9th ed, 1996) p. 51 and 57-58.*
Verma et al., Cancer Res. (1980), 40(7), 2367-71.*
Anon et al. Nutr. Rev. (1979), 37(5), 153-6.*
Oyler et al, Characerization of Autoxidation Products of Retinoic Acid, 1989, Tetrahedron, vol. 45, issue 24, pp. 7679-7694.*
Brouwer, M.S. et al., "A New Synthesis of 4-OR*-3-penten-1-ynes ($C_5$-fragment) as a Tool for The Preparation of Vitamin $A^{1\dagger}$" J. of the Royal Netherlands Chem. Soc. 98:5, 316-320 (1979).
Clark, K.B. et al., "Retinoic Acid Oxidation at High Oxygen Pressure: Evidence for Spin-Forbidden Direct Addition of Triplet Molecular Oxygen" J. Am. Chem. Soc. 119:40, 9560-9561 (1997).
R. Peto et al., "Can Dietary Beta-Carotene Materially Reduce Human Cancer Rates?", Nature (1981) 290:201-208.
N.I. Krinsky, "Actions of Carotenoids in Biological Systems", Annu. Rev. Nutr. (1993) 13:561-587.
D.L. Hill and C.J. Grubbs, "Retinoids and Cancer Prevention", Annu. Rev. Nutr. (1992) 123:161-181.
Burton and Ingold,"β: An Unusual Type of Lipid Antioxidant", Science (1984) 224:569-573.
Raphael C. Mordi, et al. "Exploratory Study of β-Carotene Autoxidation" (1991) Tetrahedron 32(33):4203-4206.
Raphael C. Mordi et al., "Oxidative Degradation of β-Carotene and β-Apo-8'-carotenal" (1993) Tetrahedron 49(4):911-928.
Alaoui-Jamali et al., "In Vivo Reversal of Doxorubicin Resistance by a New Tiapamil Analog Roll-29331", J. Pharmacol. Exp. Ther. (1993) 264(3):1229.
Pure Appl. Chem. (1985) 57:717-722, Matthews-Roth.
Oyler, Tetrahedron, vol. 45, No. 24, pp. 7679-7694, (1989).
Kanasawud, P.; Crouzet, J. C.; Mechanism of Formation of Volatile Compounds by Thermal Degradation of Carotenoids in Aqueous Medium. 2. Lycopene Degradation. J. Agric. Food Chem. 1990, 38, 1238-1242.

* cited by examiner

Primary Examiner—Sreeni Padmanabhan
Assistant Examiner—Abigail M. Cotton
(74) Attorney, Agent, or Firm—Kristina Bieker-Brady; Clark & Elbing LLP

(57) ABSTRACT

This invention features fractionated oxidized carotenoid or retinoid mixtures, and individual components thereof, which are useful as cell-differentiation-inducing, anti-proliferative, anti-metastatic and anti-tumor agents. The mixtures and compounds of the invention can be used alone or in combination with other anticancer agents for the treatment of cancer.

11 Claims, 14 Drawing Sheets

1. High molecular weight (HMW) polymers
2. Medium molecular weight (MMW) organics/oligomers
3. Low molecular weight (LMW) organics

OXIDIZED CAROTENOID FRACTIONS AND KETOALDEHYDE USEFUL AS CELL-DIFFERENTIATION INDUCERS, CYTOSTATIC AGENTS, AND ANTI-TUMOR AGENTS

CROSS REFERENCE TO RELATED APPLICATIONS

This application is a continuation-in-part of U.S. Ser. No. 09/651,250, filed on Aug. 30, 2000, now abandoned which in turn is a divisional of U.S. Ser. No. 08/527,039, filed on Sep. 12, 1995, now abandoned, which in turn is a continuation-in-part of U.S. Ser. No. 08/288,315, filed on Aug. 10, 1994, now U.S. Pat. No. 5,475,006, the disclosures of which are hereby incorporated by reference.

The field of this invention is fractionated oxidized carotenoid or retinoid mixtures, and individual components thereof, which are useful as cell-differentiation-inducing, anti-proliferative, anti-metastatic and anti-tumor agents. The mixtures and compounds of the invention can be used alone or in combination with other therapeutic agents for the treatment of cancer.

BACKGROUND OF THE INVENTION

Carotenoids and retinoids are naturally occurring substances which contain extensively conjugated polyene chains. Carotenoids have the most extensively conjugated systems of carbon-carbon double bonds which give rise to their many varied and brilliant colors. Many carotenoids and retinoids, which are naturally occurring substances, are biologically active. For example, carotenoids and retinoids have been shown to retard the development of some experimentally induced animal tumors (N. I. Krinsky, *Annu. Rev. Nutr.*, 13, 561–587 (1993); Matthews-Roth, *Curr. Top. Nutr. Dis.*, 22:17–38 (1989)). Furthermore, epidemiological evidence indicates that carotenoid intake correlates inversely with the incidence of some types of cancer (Peto et al, *Nature*, 290:201–208 (1981)). Clinical data have demonstrated that related compounds, retinoic acid, retinol and retinamides, can be used to prevent and treat cancers of the skin, head and neck, lung and bladder, acute promyelocytic leukemia, leukoplakia and myelodysplastic syndromes (see, for example, D. L. Hill and C. J. Grubs, *Annu. Rev. Nutr.*, 12:161–181 (1992)).

Carotenoids, retinoids and related conjugated polyenes are reactive towards molecular oxygen ($O_2$). β-carotene has been shown to have antioxidant properties at the low oxygen pressures found in tissues (see, for example, Burton and Ingold, *Science*, 224:569–573 (1984)). Carotenoids are more reactive than retinoids towards oxygen because of their larger, more extensively conjugated system of double bonds. The products of such oxidative degradation of carotenoids retinoids, and related conjugated polyenes and their potential physiological activities have, nevertheless, received remarkably little attention, with the exception of vitamin A, which is obtained as a product of the biological oxidation of β-carotene.

Mordi examined the products formed during the self-initiated autoxidation of β-carotene (see Mordi et al, *Tetrahedron Letters*, 32(33):4203–4206 (1991)). The main products identified in the early stages of β-carotene autoxidation, predominantly short chain carbonyl compounds, are epoxides, β-ionone, β-apo-13-carotenone, retinal, and related carbonyl compounds. The self-initiated oxidation of β-carotene with molecular oxygen has also been shown to produce epoxides, dihydrofurans, carbonyl compounds, carbon dioxide, traces of alcohols, and some other compounds (see Mordi et al, *Tetrahedron* Vol. 49(4):911–928 (1993)). The later paper, makes a mention of some polymeric/oligomeric material which frequently deposited out of solution, particularly in the later stages of β-carotene oxidation.

There exists a need for improved cancer therapeutics.

SUMMARY OF THE INVENTION

We have discovered that fractionated oxidized carotenoid mixtures-can be used as cell-differentiation-inducing, anti-proliferative, anti-metastatic and/or anti-tumor agents. A component of this mixture, 2-methyl-6-oxo-2,4-heptadienal, shares many of these properties. The mixtures and compounds of the invention can be used alone or in combination with other anticancer agents for the treatment of cancer.

In the first apect, the invention features a method of treating cancer in a patient in need thereof comprising administering to the patient a substantially pure 2-methyl-6-oxo-2,4-heptadienal in amounts effective to treat the cancer.

In the second aspect, the invention features a method of treating cancer in a patient in need thereof comprising administering to the patient a fractionated oxidized carotenoid mixture in amounts effective to treat the cancer.

Cancers to be treated using the methods of the invention include, without limitation, carcinoma of the bladder, breast, colon, kidney, liver, lung, head and neck, gall-bladder, ovary, pancreas, stomach, cervix, thyroid, prostate, or skin; a hematopoietic tumor of lymphoid lineage (i.e. leukemia, acute lymphocytic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); a hematopoietic tumor of myeloid lineage (i.e. acute myelogenous leukemia, chronic myelogenous leukemia, multiple myelogenous leukemia, myelodysplastic syndrome and promyelocytic leukemia); a tumor of mesenchymal origin (i.e. fibrosarcoma and rhabdomyosarcoma); a tumor of the central or peripheral nervous system (i.e. astrocytoma, neuroblastoma, glioma and schwannomas); melanoma; seminoma; teratocarcinoma; osteosarcoma; thyroid follicular cancer; and Kaposi's sarcoma.

Fractionated oxidized carotenoid mixtures can be used in combination with other therapeutic agents, such as anticancer agents (e.g., melphalan) for the treatment of cancer.

In another aspect, the invention provides a method of treating cancer in a patient in need thereof comprising administering to the patient a substantially pure 2-methyl-6-oxo-2,4-heptadienal in combination with another therapeutic agent. Desirably, the agent to be used in combination with 2-methyl-6-oxo-2,4-heptadienal is an anticancer agent.

Anticancer agents to be used in the methods of the present invention include alkylating agents (i.e. mechlorethamine, cyclophosphamide, ifosfamide, melphalan, chlorambucil, uracil mustard, estramustine, mitomycin C, AZQ, thiotepa, busulfan, hepsulfam, carmustine, lomustine, semustine, streptozocin, dacarbazine, cisplatin, carboplatin, or procarbazine), folic acid antagonists (i.e. methotrexate or trimetrexate), pyrimidine antagonists (i.e. fluouracil, floxuridine, cytarabine, fludarabine phosphate, or azacitidine), purine antagonists (i.e. thioguanine, mercaptopurine, cladribine, allopurine, gemcitabine, or pentostatin), antimitotic agents (i.e. vinblastine or vincristine), DNA topomerase II inhibitors (i.e. etoposide or teniposide), DNA topomerase I inhibitors (i.e. topotecan, irinotecan, camptothecin, or 9-aminocamptothecin), taxanes (i.e. paclitaxel or docetaxel), DNA intercalators (i.e. daunorubicin, doxorubicin, dactinomycin, idarubincin, plicamycin, mitomycin, amsacrine, or bleomycin), aromatase inhibitors (i.e. aminoglutethimide and anastrozole), 5-alpha-reductase inhibitors (i.e. finasteride or ketoconazole), estrogen inhibitors (i.e. tamoxifen), androgen inhibitors (i.e. flutamide), gonadotropin releasing hormone ("GRH") agonists (i.e.leuprolide or goserelin), tyrosine kinase inhibitors (i.e. Gleevec™ (Novartis), (imatinib mesylate) Leflunomide (Pharmacia), SU5416 (Pharmacia), SU6668 (Pharmacia), PTK787 (Novartis), Iressa™ (AstraZeneca), gefitinib Tarceva™, (Oncogene Science), (erlotinib hydrochloride) trastuzumab (Genentech), Erbitux™ (ImClone), (cetuximab) PKI166 (Novartis), GW2016 (GlaxoSmithKline), EKB-509 (Wyeth), EKB-569 (Wyeth), MDX-H210 (Medarex), 2C4 (Genentech), MDX-447 (Medarex), ABX-EGF (Abgenix), CI-1033 (Pfizer), Avastin™ (Genentech), (bevacizumab) IMC-1C11 (ImClone), ZD4190 (AstraZeneca), ZD6474 (AstraZeneca), CEP-701 (Cephalon), CEP-751 (Cephalon), MLN518 (Millenium), or PKC412 (Novartis)), retinoic acid derivatives (i.e. 13-cis-retinoic acid, isotretinoin, retinyl palmitate, or 4-(hydroxycarbophenyl) retinamide), hypoxia selective cytotoxins (i.e. misonidazole or nitracrine), mitotoxantrone, hydroxyurea, 1-asparginase, interferon alfa, rapamycin, CCI-779 and mitotane.

In any of the above methods, 2-methyl-6-oxo-2,4-heptadienal and a second therapeutic agent can be administered within 30 days of each other. Desirably, 2-methyl-6-oxo-2,4-heptadienal and a second anticancer agent are administered within five days of each other, 24 hours of each other, simultaneously, or they are formulated and administered together.

The present invention features a pharmaceutical pack comprising a 2-methyl-6-oxo-2,4-heptadienal and one or more additional therapeutic agents. Desirably, 2-methyl-6-oxo-2,4-heptadienal and the therapeutic agent(s) are formulated separately and in individual dosage amounts.

The present invention also features a pharmaceutical composition comprising an effective amount of 2-methyl-6-oxo-2,4-heptadienal and an therapeutic agent, together with a pharmaceutically acceptable carrier or diluent.

In still another aspect, the invention features a pharmaceutical composition comprising an effective amount of a substantially pure 2-methyl-6-oxo-2,4-heptadienal, together with a pharmaceutically acceptable carrier or diluent.

2-methyl-6-oxo-2,4-heptadienal is also useful for inhibiting the formation of metastases in a patient in need thereof, said method comprising administering to said patient 2-methyl-6-oxo-2,4-heptadienal in amounts effective to inhibit the formation of said metastases. Desirably, 2-methyl-6-oxo-2,4-heptadienal is administered in combination with another anticancer agent to inhibit the formation of metastases.

Administration of 2-methyl-6-oxo-2,4-heptadienal alone or in combination with one or more anticancer agents can be achieved by a variety of routes, such as by parenteral routes (e.g., intravenous, intraarterial, intramuscular subcutaneous injection), topical, inhalation (e.g., intrabronchial, intranasal or oral inhalation or intranasal drops), oral, rectal, or other routes.

The invention provides a convenient method of preparing 2-methyl-6-oxo-2,4-heptadienal comprising the steps of first, condensing a compound of formula IV with acetone, or its equivalent, to produce a compound of formula V:

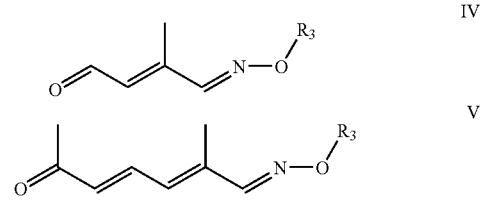

wherein $R_3$ is selected from a hydrogen atom, an alkyl of 1 to 8 carbon atoms, a heteroalkyl of 1–8 atoms, an alkene of 2–8 carbon atoms, an alkyne of 2–8 carbon atoms, or an aromatic residue; and second deprotecting the compound of formula V to produce 2-methyl-6-oxo-2,4-heptadienal.

The invention also features novel synthetic intermediates, compounds of formula V, described above.

Compounds useful in the present invention include those described herein in any of their pharmaceutically acceptable forms, including isomers such as diastereomers and enantiomers, salts, solvates, and polymorphs, thereof, as well as racemic mixtures of the compounds described herein.

By "substantially pure 2-methyl-6-oxo-2,4-heptadienal" is meant that the combined amount of β-carotene and the oxidation products of β-carotene other than 2-methyl-6-oxo-2,4-heptadienal are less than 50%, 40%, 30%, 20%, 10%, 5%, 1%, or 0.1% of the mass of 2-methyl-6-oxo-2,4-heptadienal in the substantially pure material.

By "treating" is meant to slow the spreading of the cancer, to slow the cancer's growth, to kill or arrest cancer cells that may have spread to other parts of the body from the original tumor, to relieve symptoms caused by the cancer, or to prevent cancer. The symptoms to be relieved using the combination therapies described herein include pain, and other types of discomfort.

The terms "administration" and "administering" refer to a method of giving a dosage of a pharmaceutical composition to a mammal, where the method is, e.g., topical, oral, intravenous, intraperitoneal, or intramuscular. The preferred method of administration can vary depending on various factors, e.g., the components of the pharmaceutical composition, site of the potential or actual disease and severity of disease.

By "effective amount" is meant the amount of a compound required to treat cancer. The effective amount of 2-methyl-6-oxo-2,4-heptadienal and/or anticancer agent used to practice the present invention for the treatment of cancer varies depending upon the manner of administration, the age, body weight, and general health of the subject. Ultimately, the attending physician, will decide the appropriate amount and dosage regimen. Such amount is referred to as an "effective" amount.

By "individual" or "patient" is meant any mammal.

By acetone "equivalent" is meant acetone in any protected form, including reagents which allow for the formation of compounds of formula V via a Wittig reaction.

By "alkyl" is meant a branched or unbranched saturated hydrocarbon group, desirably having from 1 to 8 carbon atoms. An alkyl may optionally include monocyclic, bicyclic, or tricyclic rings, in which each ring desirably has three to six members. The alkyl group may be substituted or unsubstituted. Exemplary substituents include alkoxy, aryloxy, sulfhydryl, alkylthio, arylthio, halogen, hydroxyl, fluoroalkyl, perfluoroalkyl, amino, aminoalkyl, disubstituted amino, quaternary amino, hydroxyalkyl, carboxyalkyl, and carboxyl groups.

By "alkene" is meant a branched or unbranched hydrocarbon group containing one or more double bonds, desirably having from 2 to 8 carbon atoms. An alkene may optionally include monocyclic, bicyclic, or tricyclic rings, in which each ring desirably has five or six members. The alkene group may be substituted or unsubstituted. Exemplary substituents include alkoxy, aryloxy, sulfhydryl, alkylthio, arylthio, halogen, hydroxyl, fluoroalkyl, perfluoroalkyl, amino, aminoalkyl, disubstituted amino, quaternary amino, hydroxyalkyl, carboxyalkyl, and carboxyl groups.

By "alkyne" is meant a branched or unbranched hydrocarbon group containing one or more triple bonds, desirably having from 2 to 8 carbon atoms. An alkyne may optionally include monocyclic, bicyclic, or tricyclic rings, in which each ring desirably has five or six members. The alkyne group may be substituted or unsubstituted. Exemplary substituents include alkoxy, aryloxy, sulfhydryl, alkylthio, arylthio, halogen, hydroxyl, fluoroalkyl, perfluoroalkyl, amino, aminoalkyl, disubstituted amino, quaternary amino, hydroxyalkyl, carboxyalkyl, and carboxyl groups.

By "heteroalkyl" is meant a branched or unbranched group in which one or more methylenes ($-CH_2-$) are replaced by nitrogen, oxygen, sulfur, carbonyl, thiocarbonyl, phosphoryl, sulfonyl, or NR, where R is an alkyl. Some examples include tertiary amines, ethers, thioethers, amides, thioamides, carbamates, thiocarbamates, phosphoramidates, sulfonamides, and disulfides. A heteroalkyl may optionally include monocyclic, bicyclic, or tricyclic rings, in which each ring desirably has three to six members. The heteroalkyl group may be substituted or unsubstituted. Exemplary substituents include alkoxy, aryloxy, sulfhydryl, alkylthio, arylthio, halogen, hydroxyl, fluoroalkyl, perfluoroalkyl, amino, aminoalkyl, disubstituted amino, quaternary amino, hydroxyalkyl, carboxyalkyl, and carboxyl groups.

By "aromatic residue" is meant an aromatic group having a ring system with conjugated π electrons (e.g., phenyl, or imidazole). The ring of the aryl group is preferably 5 to 10 atoms. The aromatic ring may be exclusively composed of carbon atoms or may be composed of a mixture of carbon atoms and heteroatoms. Preferred heteroatoms include nitrogen, oxygen, sulfur, and phosphorous. Aryl groups may optionally include monocyclic, bicyclic, or tricyclic rings, where each ring has preferably five or six members. The aryl group may be substituted or unsubstituted. Exemplary substituents include alkyl, hydroxyl, alkoxy, aryloxy, sulfhydryl, alkylthio, arylthio, halogen, fluoroalkyl, carboxyl, carboxyalkyl, amino, aminoalkyl, monosubstituted amino, disubstituted amino, and quaternary amino groups.

By "fluoroalkyl" is meant an alkyl group that is substituted with a fluorine.

By "perfluoroalkyl" is meant an alkyl group consisting of only carbon and fluorine atoms.

By "carboxyalkyl" is meant a chemical moiety with the formula $-(R)-COOH$, wherein R is an alkyl group.

By "hydroxyalkyl" is meant a chemical moiety with the formula $-(R)-OH$, wherein R is an alkyl group.

By "alkoxy" is meant a chemical substituent of the formula $-OR$, wherein R is an alkyl group.

By "aryloxy" is meant a chemical substituent of the formula $-OR$, wherein R is an aryl group.

By "alkylthio" is meant a chemical substituent of the formula $-SR$, wherein R is an alkyl group.

By "arylthio" is meant a chemical substituent of the formula $-SR$, wherein R is an aryl group.

DETAILED DESCRIPTION OF THE INVENTION

The invention provides methods of treating cancer, allowing for improved cancer therapy while permitting lower doses of anticancer agents to be used. Other features and advantages of the invention will be apparent from the following detailed description, and from the claims.

Fractionated Oxidized Carotenoid Mixtures

Chemistry

Figure 1:
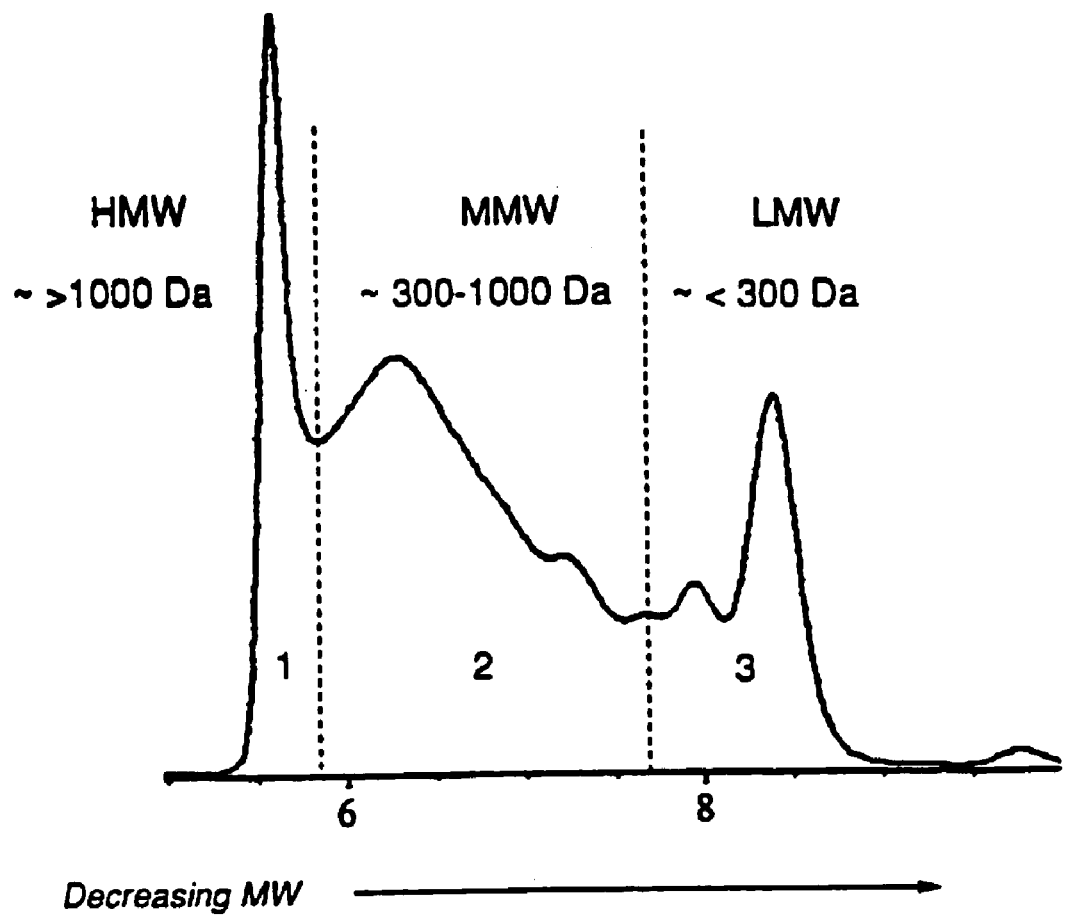
FIG. 1 is a chromatogram illustrating the molecular weight split of the main fractions of the invention.

Carotenoids, such as β-carotene, lycopene, retinoic acid and canthaxanthin, can be oxidized using the methods disclosed in U.S. Pat. No. 5,475,006, hereby incorporated by reference. The resulting mixture, and certain fraction thereof, are biologically active against tumors. The fractionation evolved through three phases. The three separation schemes, 3–4 levels deep, are depicted below:

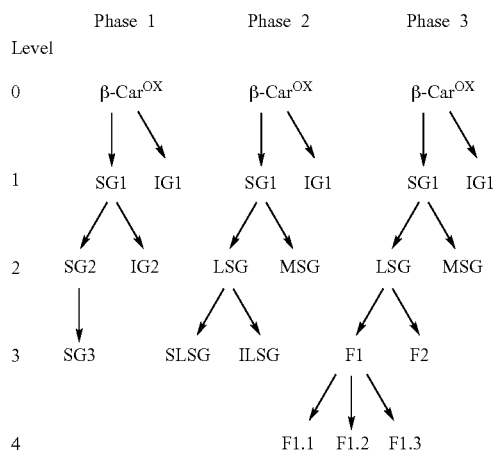

β-Car$^{OX}$ was synthesized using a procedure very similar to that described in U.S. Pat. No. 5,475,006. Briefly, β-carotene (30 g) dissolved in benzene (3.0 L; 0.02 M) was stirred for 4 days at room temperature under an atmosphere of oxygen. GPC chromatography confirmed the presence of three major components, i.e., the low (<300 Da), medium (300–1000 Da), and high (>1000 Da) MW fractions (see FIG. 1).

Level 1 Separation (Phases 1–3)

Figure 2:
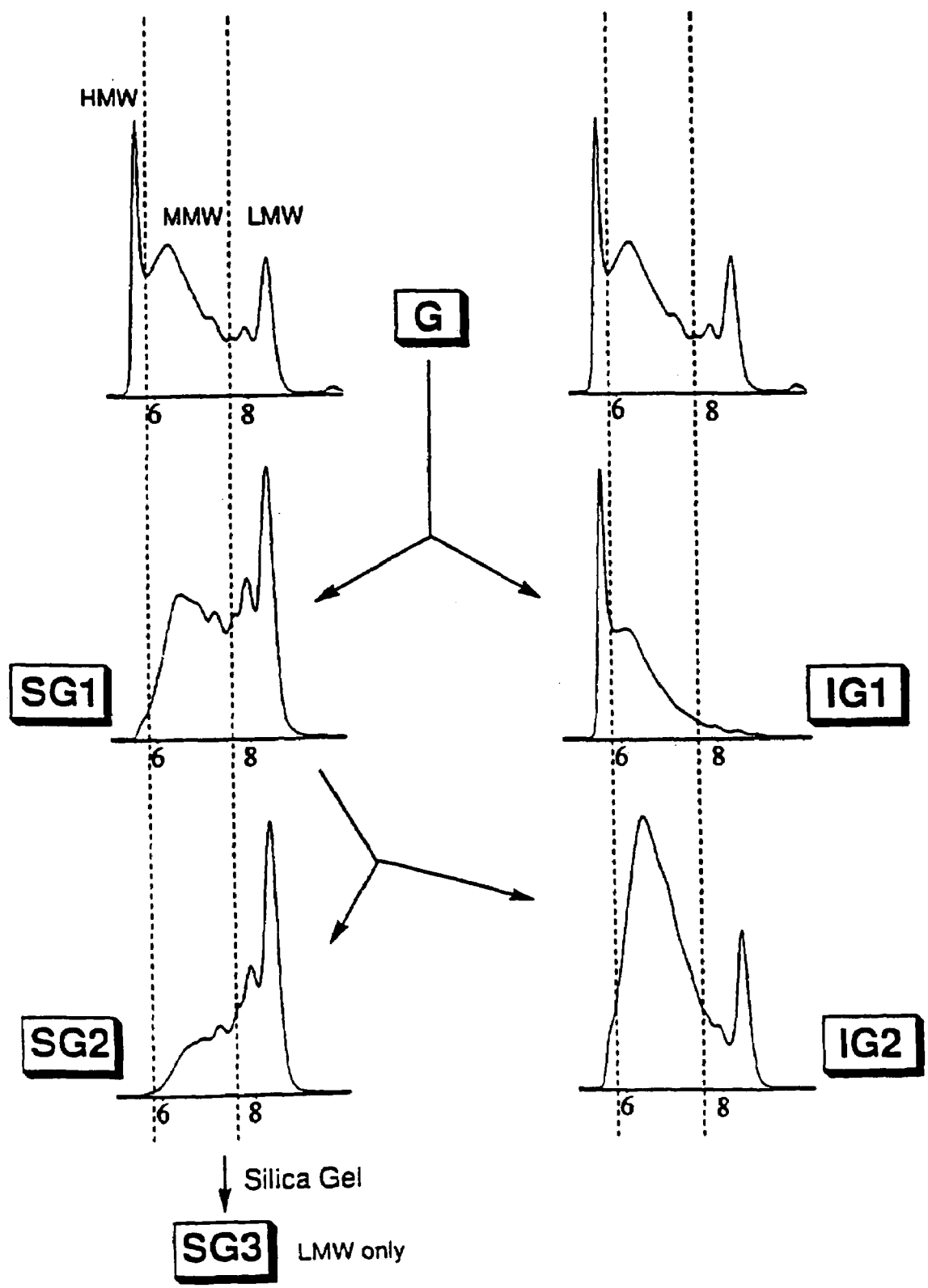
FIG. 2 is a series of chromatograms illustrating schematically the three-level solvent mediated fractionation of the mixture.

The solution (3.0 L) was concentrated to ca. 200 mL and then diluted with approximately 2 L of hexane. The precipitate, IG1, ca. 65% of the total mixture, contained most of the high MW material (>1000 Da). The supernatant containing the soluble fraction, i.e., the low (<300 Da) and medium (300–1000 Da) MW fractions and practically none of the high MW fraction (see FIG. 2), was evaporated to dryness to give a residue, SG1.

Level 2 Separation (Phase 1)

Fraction SG1 (1.2 g) was stirred in hexane (120 mL) at room temperature for 30 minutes. The insoluble fraction, IG2, that was filtered off, contained mostly medium MW and some low MW material (see FIG. 1). The supernatant containing the soluble fraction was evaporated to yield SG2, containing mostly low MW and some medium MW material (see FIG. 2).

Level 2 Separation (Phases 2 and 3)

Figure 3:
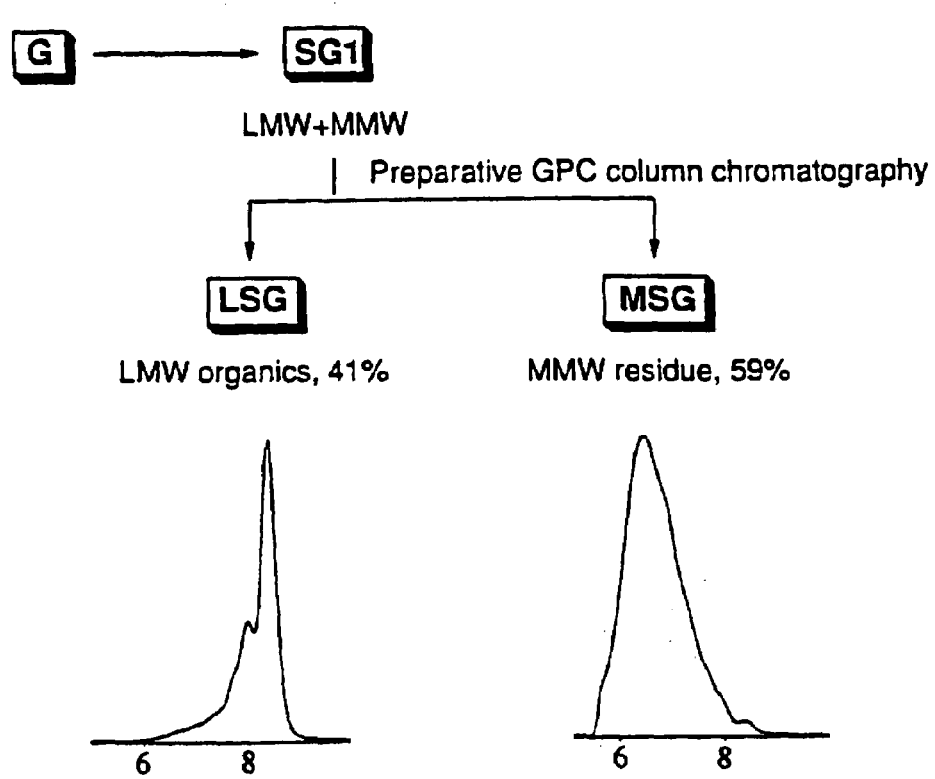
FIG. 3 is a flow chart illustrating the GPC chromatogram of a preparative GPC separation of fraction SG1 into fractions LSG and MSG.
Figure 3:
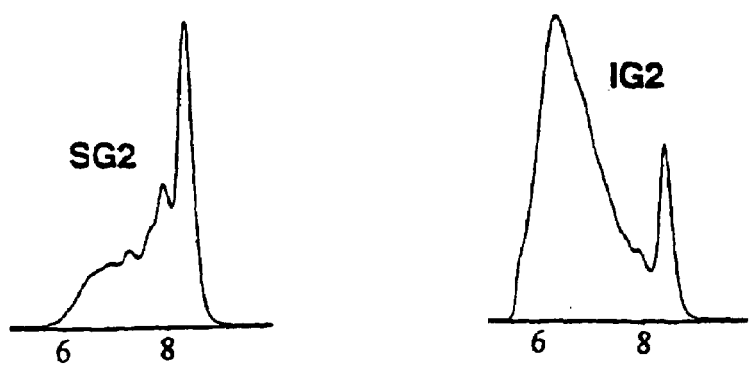

Fraction SG1 (10 g) dissolved in tetrahydrofuran (10 ml) was separated into low and medium MW fractions, LSG (40%) and MSG (55%), respectively, by successive injections of samples (250 µL) onto a preparative-scale GPC chromatography column (19×300 mm, Waters styragel, 15 µm particle size, 10 nm pore size) and elution with tetrahydrofuran (4 mL/minute). A clean separation into two MW fractions was obtained as illustrated, in FIG. 3.

Level 3 Separation (Phase 1)

Fraction SG2 (688 mg) was loaded onto a silica gel column and eluted with hexane/ethyl acetate (95:5). The eluted fractions were combined and the solvent removed to give fraction SG3.

Level 3 Separation (Phase 2)

Fraction LSG (600 mg) was stirred with ice-cold pentane (1 mL) for 1 minute and then most of the supernatant was decanted off. This procedure was repeated four times. The insoluble fraction, ILSG, was filtered and the solvent was evaporated from the combined supernatant fractions containing the soluble component, giving fraction SLSG.

Level 3 Separation (Phase 3)

Figure 4A:
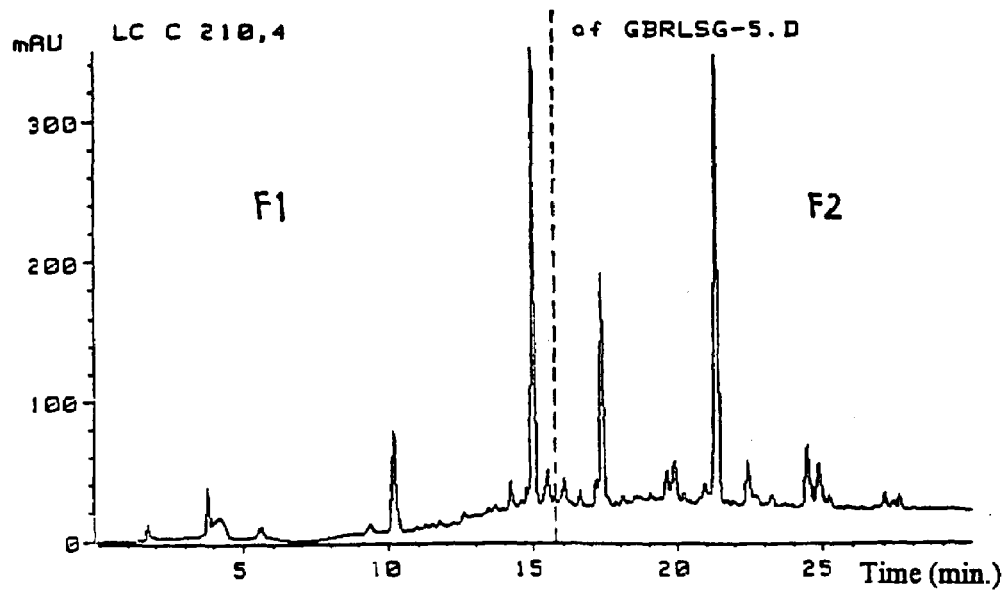
FIGS. 4a and 4b are HPLC chromatograms of fraction LSG, monitored at 219 and 265 nm, respectively, and show how fraction LSG was split into fractions F1 and F2.
Figure 4B:
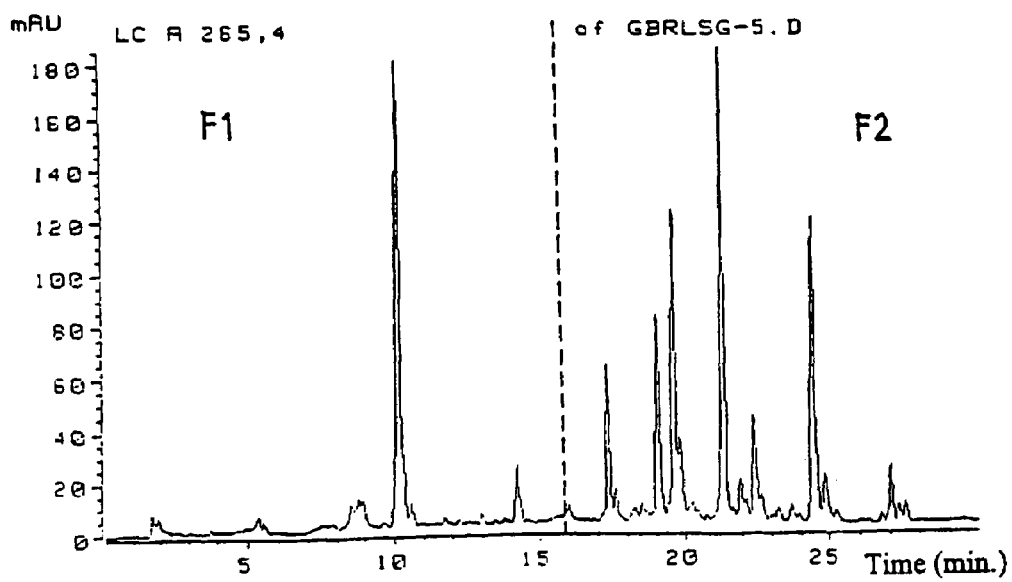

Fraction LSG (4.4 g), dissolved in acetonitrile (10 mL), was separated into two fractions by successive injections (450 µL; total 9.0 mL) onto a preparative-scale HPLC instrument equipped with three Waters NovaPak HR C18 (reverse phase, 6 µm particle size, 6 nm pore size) PrepPak cartridges (40×100 mm) connected in series and eluted with acetonitrile (40 mL/minute). Fractions F1 (80%) and F2 (20%) were obtained by collecting eluent from 4.8 to 6.4 minutes and 6.4 to 12 minutes, respectively. The dotted vertical line in the middle of the analytical high performance liquid chromatography (HPLC) chromatogram in FIG. 4 shows how LSG was divided into the two new fractions, F1 and F2. The elution times of compounds in FIG. 4 and the corresponding division time are different from those in the preparative HPLC because of differences in the conditions necessary to obtain optimal separations under analytical and preparative conditions, respectively.

Level 4 Separation (Phase 3)

Figure 5A:
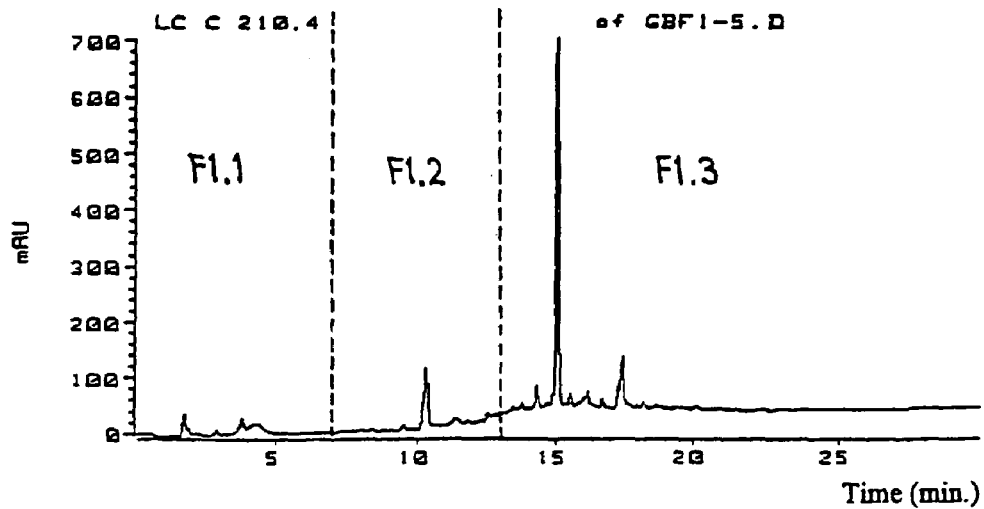
FIGS. 5a and 5b are HPLC chromatograms of fraction F1, monitored at 219 and 265 nm, respectively, and show how fraction F1 was split into fractions F1.1 and F1.2 and F1.3.
Figure 5B:
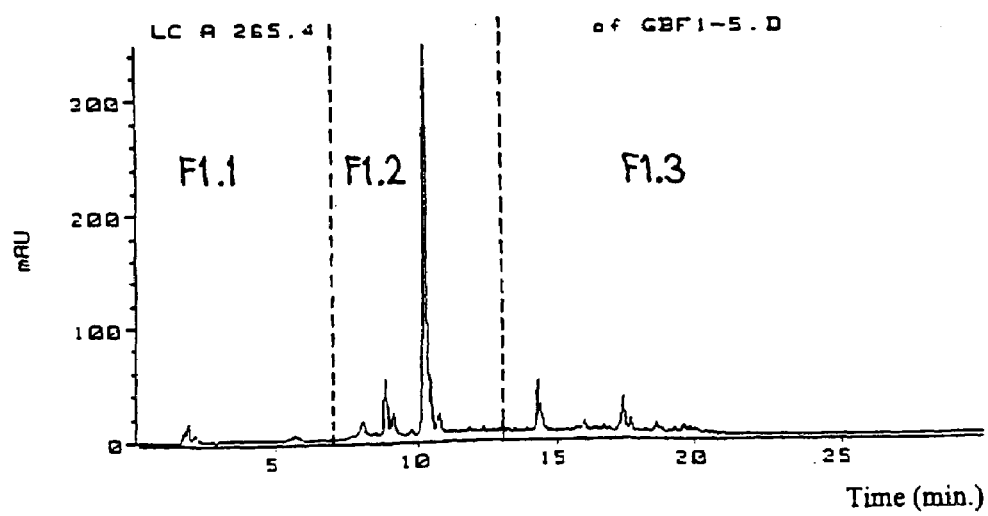
Figure 6A:
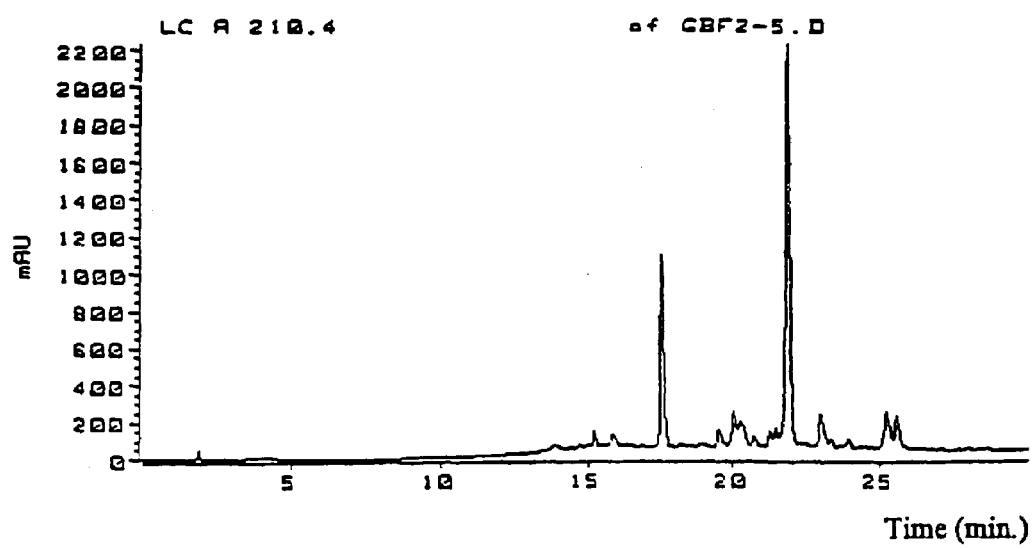
FIGS. 6a and 6b are chromatograms of fraction F2, monitored at 219 and 265 nm, respectively.
Figure 6B:
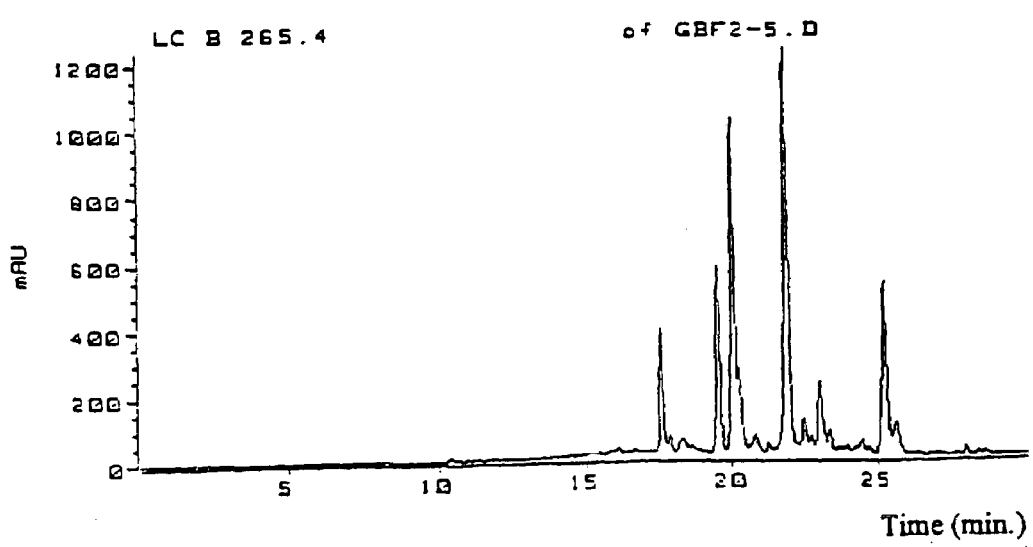

Fraction F1 (700 mg) dissolved in acetonitrile (1.5 mL), was separated into three fractions, F1.1 (11%), F1.2 (13%) and F1.3 (5%), by successive injections (250 µL; total 1.25 mL) onto a preparative-scale HPLC instrument equipped with the same column already described and eluted with a 50:45:5 mixture of water, acetonitrile and methanol at a flow rate of 40 mL/minute The fractions were obtained by collecting eluent from 2.0 to 6.6 minutes, 6.6 to 12.0 minutes and 12.0 to 23 minutes, respectively. The dotted vertical lines in FIG. 5 show how the cuts were made to obtain the three fractions.

Chemical Compositions

Figure 7:
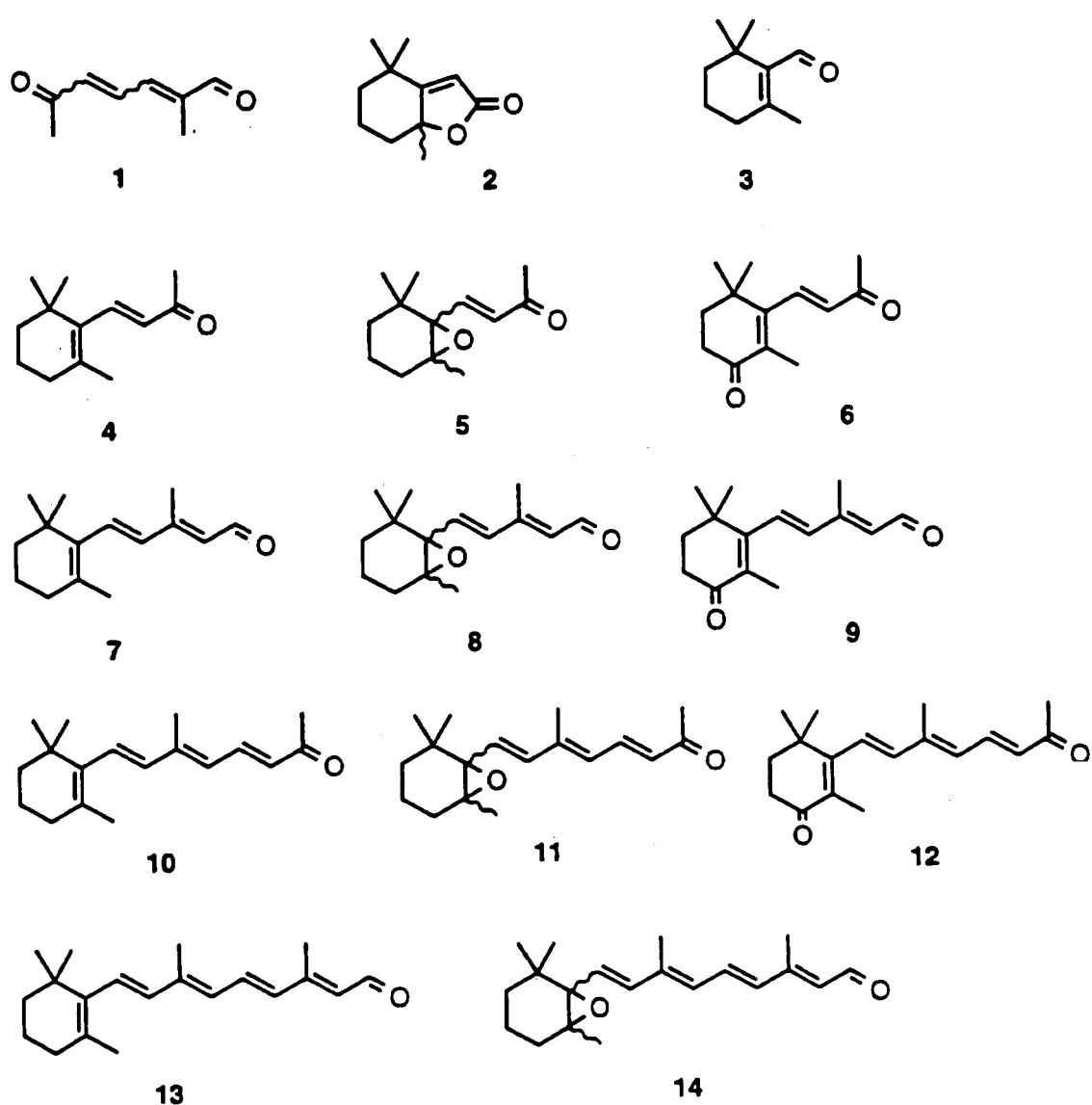
FIG. 7 is a table of the formulae of specific compounds identified in the fractions of the invention.

Structures of the numbered compounds are provided in FIG. 7. Fractions F1.1, F1.2, and F1.3 each contain only a few compounds as FIG. 5 indicates. A major component in F1.2 is 2-methyl-6-oxo-2,4-heptadienal (compound 1, referred to elsewhere in the text as "the ketoaldehyde"). Dihydroactinidiolide (compound 2) is a major component of F1.3. Compounds 3–14 have been identified in fraction F2. These are β-cyclocitral (3), β-ionone (4), 1-ionone 5,6-epoxide (5), 4-oxo-β-ionone (6), β-ionylidene acetaldehyde (7), β-ionylidene acetaldehyde 5,6-epoxide (8), 4-oxo-β-ionylidene acetaldehyde (9), β-apo-13-carotene (10), β-apo-13-carotene 5,6-epoxide (11), 4-oxo-β-apo-13-carotene (12), retinal (13), and retinal 5,6-epoxide (14).

Biology

In vitro biological assays were carried out by testing for cytostatic activity, induction of differentiation, and the effect upon the cell cycle. In vivo tests were carried out by testing for inhibition of growth of tumors in mice.

In Vitro Tests

Fractions were tested for cytostatic properties and ability to induce differentiation. The results were compared with those obtained for β-Car$^{OX}$, which served as a reference indicating whether or not fractionation was leading to fractions with enhanced activity. Retinoic acid and/or β-carotene were used as controls in some of the cell lines tested in order to differentiate their effects from that of β-Car$^{OX}$. All of the samples were tested in identical 'by weight' concentrations. Comparisons have been done on a pseudo molarity scale by dividing the weight of sample used by the molecular weight of β-carotene (537 Da). Fractions were tested in human colon carcinoma (HCT116), human neuroblastoma (IMR32), human acute promyelocytic leukemia (NB4), human chronic myelogenous leukemia (K562), and mouse keratinocytes (Balb/c/MK).

Cytostatic Effects

Figure 8A:
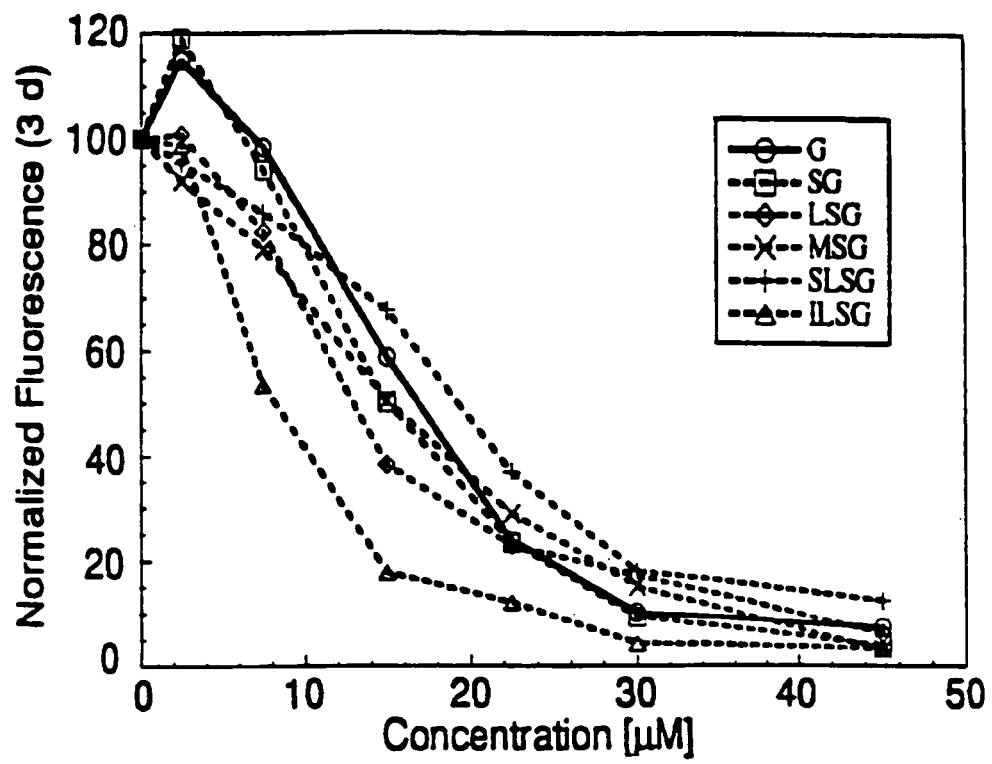
FIG. 8a is a graph showing the cytostatic effect of certain fractions of the invention on a colon cancer cell line.
Figure 8B:
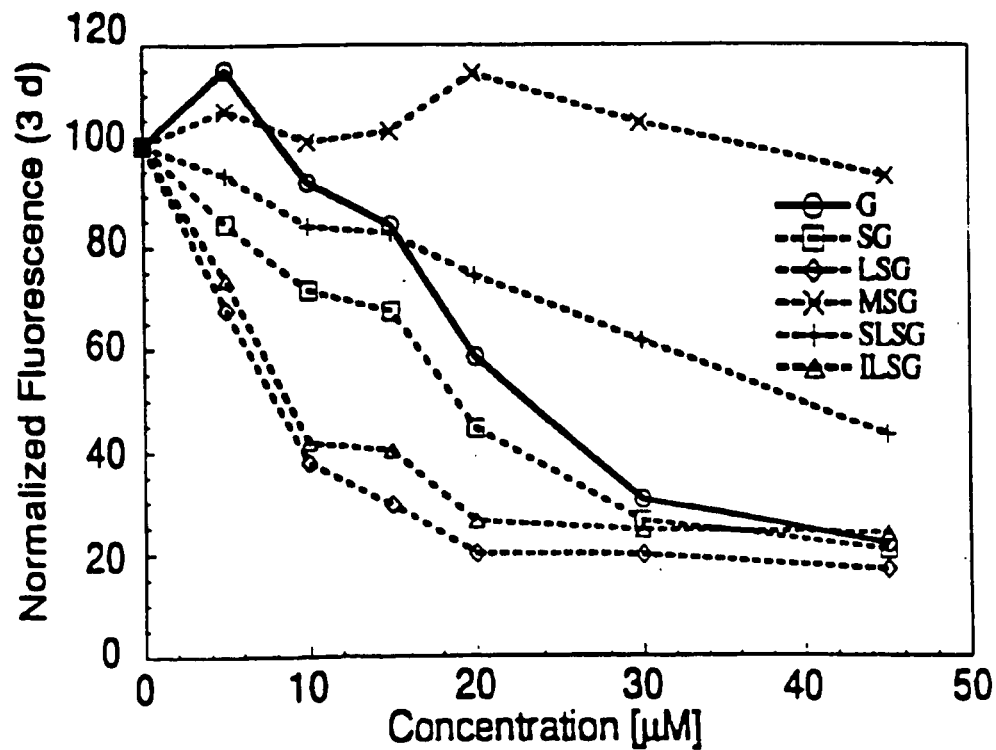
FIG. 8b is a graph showing the cytostatic effect of certain fractions of the invention on a leukemic cell line.

Cells were treated with six concentrations of each sample (2.5, 7.5, 15, 22.5, 30, and 45 µM for HCT116 and IMR32 and 2.5, 5, 7.5, 10, 15, 22.5 µM for NB4 and K562 cell lines. After 3 days, the cells were lysed, incubated with Hoechst dye 33258 and fluorescence of the solution was measured to provide a measure of cellular DNA present. The fluorescence data for each substance tested were collected and divided by the corresponding values for untreated cells, after correcting for the background fluorescence, to determine the cytostatic effect for each sample concentration. FIGS. 8a and 8b illustrate results that were obtained for the HCT116 human colon cancer and the K562 human leukemia cell lines, respectively.

It is apparent that relative activity can depend very much upon the cell line chosen. This is illustrated particularly well by fraction MSG, which is active in the HCT116 cell line but is inactive in the K562 line, whereas fraction ILSG is highly active in both lines (more so than $\beta\text{-Car}^{OX}$). These observations imply that the cytostatic effect can be obtained through the action of more than one compound.

Table 1 summarizes the results that were obtained for the four cell lines. Fractions have been ranked relative to $\beta\text{-Car}^{OX}$ by dividing each growth inhibition value at each sample concentration by the corresponding $\beta\text{-Car}^{OX}$ value and determining qualitatively by inspection the trends across the six sample concentrations. Activities of fractions are expressed as "+", "0", and "−", indicating activity higher, similar to, and less than the activity of $\beta\text{-Car}^{OX}$, respectively.

Surprising is the apparent diminution of activity in the simpler fractions at more advanced levels of fractionation (3 and 4) following an enhancement of activity in their more complex parent fractions at preceding levels (1 and 2), e.g., fractions F1, F2, F1.2 and F1.3. The later, simpler fractions should, in principle, be enriched in active components, leading to the expectation of higher activity. It is possible that the higher activity observed in the earlier, more complex fractions derives from the presence of more than one active compound and/or from synergistic relations between two or more compounds.

TABLE 1

Cytostatic Effect On Cell Lines

| Level | Fraction | Cell Lines | | | |
|---|---|---|---|---|---|
| | | HCT116 | IMR32 | K562 | NB4 |
| 0 | $\beta\text{-Car}^{OX}$ | 0 | 0 | 0 | 0 |
| 1 | SG1 | 0 | + | + | + |
| | IG1 | + | 0 | 0 | + |
| 2 | SG2 | + | + | + | + |
| | IG2 | + | + | + | + |
| | LSG | − | 0 | + | 0 |
| | MSG | 0 | 0 | − | 0 |
| 3 | SG3 | + | + | + | 0 |
| | F1 | − | 0 | 0 | 0 |
| | F2 | 0 | 0 | 0 | − |
| 4 | F1.1 | − | 0 | + | + |
| | F1.2 | − | 0 | 0 | 0 |
| | F1.3 | − | 0 | 0 | 0 |
| | β-Carotene | − | 0 | − | − |
| | All trans Retinoic Acid | − | + | 0 | 0 |

Cell Differentiation

The cell differentiation-inducing effects of the fractions were determined qualitatively by observation of morphological changes in cell lines and quantitatively by measuring the expression of characteristic protein markers using monoclonal antibodies and flow cytometry. In Table 2, active fractions are denoted by the "+" symbol and highly active fractions are denoted by a "++".

There is widespread activity among the fractions in the IMR32 human neuroblastoma cell line. Unexpectedly, three pairs of fractions (SG1 and IG1, SG2 and IG2, and LSG and MSG) show an unprecedented ability to induce differentiation towards two different phenotypes from the same precursor cell line. That is, it is possible to direct the IMR32 cell line towards glial or neuronal cells, depending on the choice of fraction. The ability to induce formation of neurons disappears in the later, simpler fractions, such as those of stage 4. These observations are further evidence that $\beta\text{-Car}^{OX}$ contains multiple active compounds possessing different types of activity.

Differentiation induction in the NB4 human leukemia cell line is confined to the early and chemically complex IG2 and MSG fractions which are strongly active. Only one fraction, SG3, potentiates differentiation in the quasi-normal L6 rat myoblast cell line.

The greater activity in the transformed cell lines, particularly IMR32, compared to the quasi-normal L6 line provides support for the strategy of using selective differentiation of transformed cells to control cancerous cell growth in a nontoxic manner.

TABLE 2

Differentiation Induction

| Level | Fraction | Cell Lines | | |
|---|---|---|---|---|
| | | HCT116 | IMR32 | NB4 |
| 1 | SG1 | +(n) | ne | ne |
| | IG1 | +(g) | ne | ne |
| 2 | SG2 | +(n) | ne | ne |
| | IG2 | +(g) | ++ | ne |
| | LSG | ++(n) | ne | ne |
| | MSG | ++(g) | ++ | ne |
| 3 | SG3 | +(n) | ne | ++ |
| | F1 | +(n) | ne | ne |
| | F2 | ++(n) | ne | ne |
| 4 | F1.1 | ++(g) | ne | ne |
| | F1.2 | ne | ne | ne |
| | F1.3 | ne | ne | ne | ne = no effect.
(g) = differentiation toward glial phenotypes.
(n) = differentiation toward neuronal phenotypes.

Qualitative data were provided in the first phase of research for the differentiation-inducing effect of $\beta\text{-Car}^{OX}$ upon the mouse Balb/c/MK keratinocyte cell line. Table 3 provides supporting qualitative data.

TABLE 3

Expression of Cytokeratines in Balb/c/MK Keratinocytes

| Measurement | Sample | A | $I_A$ |
|---|---|---|---|
| Expression of Cytokeratins 1 and 10 | Control | 90.3 | 4.4 |
| | $Ca^{++}$ (1.8 mM) | 96.5 | 13.8 |
| | Retinoic Acid (3 µM) | 94.5 | 15.4 |
| | $\beta\text{-Car}^{OX}$ (30 µM) | 96.5 | 7.9 |
| Expression of a panel (CAMON) | Control | 93.7 | 60.7 |
| | $Ca^{++}$ (1.8 mM) | 97.6 | 87.2 |

TABLE 3-continued

Expression of Cytokeratines in Balb/c/MK Keratinocytes

| Measurement | Sample | A | $I_A$ |
|---|---|---|---|
| of Cytokeratins | Retinoic Acid (3 μM) | 94.3 | 129.8 |
| | β-Car$^{OX}$ (30 μM) | 96.2 | 82.1 |

A is the percentage of immunopositive cells expressing the indicated cytokeratins. Column $I_A$ represents the intensity of expression per cell (arbitrary units).

Cytokeratins 1 and 10 are high molecular weight proteins which are increasingly expressed with the progression of the differentiation program. In vitro cell cultures, the differentiation is classically induced by exposure to culture media containing high levels of calcium. Cells cultured in low calcium media remain proliferative. As illustrated in Table 3, retinoic acid can substitute for $Ca^{++}$ in increasing expression of cytokeratins 1 and 10. β-Car$^{OX}$ also can substitute for calcium in inducing Balb/c/MK keratinocyte differentiation. The apparently smaller effect of β-Car$^{OX}$ compared to retinoic acid is due not to lower potency but to a delayed action and similar results are obtained using a panel of other cytokeratins (Cytokeratin coctail from CAMON containing cytokeratins 1–8, 10, 13, 14, 15, 16, 19).

Cell Cycling

The distribution of the β-Car$^{OX}$-treated cell population among the three phases of the cell cycle G1 phase (resting cells), S phase (DNA synthesis stage), and G2 phase (chromosome doubling stage) shows an accumulation of cells in the S phase. There is no G1 block. This effect is due to a lengthening of the duration of the cell cycle. It was found that the β-Car$^{OX}$-treated NB4 cells completed a cell cycle in 36 hours whereas the duration of the cell cycle in controls and retinoic acid-treated matching samples was 22 hours and 18 hours, respectively. The data were acquired using flow cytometry analysis of the individual intracellular DNA content of cells from synchronized populations. Sampling was done every 5 hours over a period of 48 hours. Furthermore, the accumulation of cells in the S phase was observed in L6 myoblasts as well.

β-Car$^{OX}$ in Combination with Retinoic Acid

Given the cell differentiation-inducing properties of β-Car$^{OX}$ and some of its fractions, it is instructive not only to compare the effects obtained with those of the better known all-trans retinoic acid, which is recognized as being able to regulate differentiation capacities of several mammalian cell types, but to determine also the effect upon cells when β-Car$^{OX}$ and retinoic acid are used together. Table 4 presents qualitative data illustrating the results obtained with various combinations of β-Car$^{OX}$ and retinoic acid in both the NB4 and IMR32 cell lines.

When an equipotent concentration of β-Car$^{OX}$ is combined with retinoic acid, their differentiation-inducing effects cancel out. However, when the concentration of either one of them is increased relative to the other, differentiation-induction is restored. Surprisingly, when the concentration of both agents together is raised, significant enhancement of differentiation is observed.

Many differentiation markers are expressed transiently during the differentiation program. In the NB4 cell line, protein CD33 is associated with early stages of differentiation, followed by protein CD11b, an intermediate marker, and eventually by protein CD15, an advanced differentiation marker. Enhanced differentiation therefore will be characterized by a decrease in the expression and intensity of the CD33 marker and an increase in expression and intensity of the CD15 marker.

TABLE 4

Differentiating Properties of Combinations of β-Car$^{OX}$ and Retinoic Acid in NB4 and IMR32 Cell Lines

| Retinoic Acid | β-Car$^{OX}$ | Differentiation |
|---|---|---|
| L<br>(NB4, 0.1–1 μM)<br>(IMR32, 1–2.5 μM) | — | yes |
| — | L<br>(NB4, 1–5 μM)<br>(IMR32, 3–9 μM) | yes |
| L<br>(NB4, 0.1–1 μM)<br>(IMR32, 1–2.5 μM) | L<br>(NB4, 1–5 μM)<br>(IMR32, 3–9 μM) | no |
| H<br>(NB4, 1–10 μM)<br>(IMR32, 5–10 μM) | L<br>(NB4, 1–5 μM)<br>(IMR32, 3–9 μM) | yes |
| L<br>(NB4, 0.1–1 μM)<br>(IMR32, 1–2.5 μM) | H<br>(NB4, 5–10 μM)<br>(IMR32, 5–10 μM) | yes |
| H<br>(NB4, 1–10 μM)<br>(IMR32, 5–10 μM) | H<br>(NB4, 5–10 μM)<br>(IMR32, 5–10 μM) | yes (enhanced) |

L and H indicate low and high concentration as defined above. A dash indicates the absence of the agent.

Table 5 presents quantitative data on the effect of all-trans retinoic acid, β-Car$^{OX}$ and some of its fractions on the level of expression of these specific differentiation markers in NB4 cells, supplemented either with individual fractions or various binary combinations containing all-trans retinoic acid. The results indicate that β-Car$^{OX}$ is not as effective as retinoic acid (β-Car$^{OX}$ requires more time to fully express its effect). Combined treatment with retinoic acid and β-Car$^{OX}$, or some of its fractions, results in inhibition of differentiation (an antagonistic effect) as has been already noted above for β-Car$^{OX}$ (Table 4), but with fraction IG2 differentiation proceeds further than with either IG2 or retinoic acid alone (a cooperative effect).

This finding that β-Car$^{OX}$ and some of its fractions can both interfere with and enhance the action of retinoic acid implies that, because retinoic acid operates through and interacts with the superfamily of nuclear receptors (including the retinoid, thyroid hormone, vitamin $D_3$, and orphan receptors), β-Car$^{OX}$ and some of its fractions are specifically targeting this family of receptors and affecting the cell at the level of nuclear DNA transcription.

The enhancement of differentiation obtained under certain conditions indicated above offers the prospect that an appropriate combination of retinoic acid and β-Car$^{OX}$ or the fraction IG2 will be a more effective therapy than retinoic acid alone. There is particular relevance to this because retinoic acid is used for the treatment of acute promyelocytic leukemia (APL), despite the fact that it provides only 5–6 months of remission before it becomes ineffective in treating the resurgent cancer. Our results support the possibility that a combination of two agents, particularly those indicated above, will push leukemic cells more fully down a terminal differentiation path, increasing the likelihood that their return to a proliferative state is blocked.

TABLE 5

Expression of Differentiation Markers in the NB4 Cell Line at Five Days

| | Expression Markers | | | | | | | | | | | |
|---|---|---|---|---|---|---|---|---|---|---|---|---|
| | CD33 | | | | CD11b | | | | CD15 | | | |
| Sample | A | B | $I_A$ | $I_B$ | A | B | $I_A$ | $I_B$ | A | B | $I_A$ | $I_B$ |
| RA | 87.1 | — | 1.6 | — | 71.9 | — | 2.6 | — | 73.1 | — | 73.1 | — |
| β-Car$^{OX}$ | 95.8 | — | 4.8 | — | 73.8 | — | 1.0 | — | 32.1 | — | 32.1 | — |
| SG1 | 96.9 | — | 5.2 | — | 77.3 | — | 0.8 | — | 30.0 | — | 30.0 | — |
| IG1 | 94.6 | — | 5.0 | — | 71.5 | — | 1.0 | — | 28.7 | — | 28.7 | — |
| SG2 | 95.3 | — | 4.6 | — | 72.1 | — | 1.2 | — | 29.4 | — | 29.4 | — |
| IG2 | 87.8 | — | 4.6 | — | 54.6 | 10.9 | 1.3 | 4.5 | 15.0 | 30.0 | 15.0 | 4.1 |
| SG3 | 64.2 | — | 1.7 | — | 29.1 | — | 2.0 | — | 19.2 | — | 19.2 | — |
| β-Car$^{OX}$ + RA | 39.8 | — | 1.6 | — | 11.6 | — | 2.1 | — | 23.6 | — | 23.6 | — |
| SG1 + RA | 35.1 | 15.5 | 0.7 | 3.1 | 31.7 | — | 1.6 | — | 64.7 | — | 64.7 | — |
| SG2 + RA | 45.4 | 21.4 | 1.0 | 7.1 | 59.8 | — | 1.0 | — | 75.1 | — | 75.1 | — |
| IG2 + RA | 71.6 | — | 1.1 | — | 80.2 | — | 1.9 | — | 83.7 | — | 83.7 | — |

The combined treatments were 1 μM RA and 7.5 μM β-Car$^{OX}$, or its fractions. Columns A and B represent the percentage of immunopositve (those bearing differentiation markers) cells in the total population. Column B values correspond to the emergence of a distinct cell population in terms of differention as determined by theintensity of the marker expression. Columns $I_A$ and $I_B$ correspond to the average intensities of the differentiation marker expression per cell (arbitrary units).

The hypothesis that β-Car$^{OX}$ is affecting the cell at the level of nuclear DNA transcription through the interactions with the above mentioned family of receptor is further supported by the results of combined treatment of another cell line, IMR32, with retinoic acid and β-Car$^{OX}$. As in the case of NB4, antagonistic or synergistic effects (depending on the concentrations of both agents) can be observed (see Table 6). For example, the expression of neuorofilament, NF (a marker indicating that the cells differentiated into neurons), is maximized at 1 μM RA and 5 μM β-Car$^{OX}$ when each is used alone. When used together at these concentrations they cancel each other out and the expression of NF is similar to that of the control (i.e., antagonism). However, when the concentration of RA is increased to 2.5 μM and the concentration of β-Car$^{OX}$ is reduced to 3 μM, the expression of NF is higher then for either of them alone (i.e., cooperation). Expression of glial fibrillary acidic protein, GFAP, is a useful marker indicating differentiation towards glial cells. Both RA and β-Car$^{OX}$ enhance the expression of GFAP, but the effect is subject to complex interactions of the two agents. For example, whereas retinoic acid itself is most effective at low concentration of 1 μM, the presence of β-Car$^{OX}$ increases this optimal concentration up to 10 μM depending on the concentration of β-Car$^{OX}$ (see table 6).

TABLE 6

Expression of NF and GFAP Markers in the IMR32 Cell Line.

| RA | β-Car$^{OX}$ | NF | | GFAP | |
|---|---|---|---|---|---|
| (μM) | (μM) | % | intensity | % | intensity |
| 0 | 0 | 96.0 | 4.3 | 65.0 | 1.7 |
| 1.0 | 0 | 96.4 | 14.2 | 94.4 | 18.4 |
| 2.5 | 0 | 97.2 | 11.9 | 90.5 | 6.1 |
| 5.0 | 0 | 95.5 | 8.4 | 87.5 | 5.2 |
| 10.0 | 0 | 92.0 | 7.9 | 83.1 | 4.0 |
| 0 | 3 | 90.6 | 7.7 | 91.5 | 5.2 |
| 0 | 5 | 98.7 | 53.0 | 87.0 | 5.2 |
| 0 | 7.5 | 96.1 | 8.6 | 94.2 | 8.7 |
| 0 | 10 | 95.8 | 8.5 | 88.1 | 4.5 |
| 1.0 | 3 | 94.1 | 6.4 | 98.2 | 22.4 |
| 1.0 | 5 | 94.7 | 7.5 | 87.4 | 5.6 |
| 1.0 | 7.5 | 98.2 | 17.6 | 89.7 | 6.2 |
| 2.5 | 10 | 98.3 | 70.0 | 87.7 | 5.6 |
| 2.5 | 3 | 94.7 | 7.2 | 97.9 | 21.7 |
| 2.5 | 5 | 98.7 | 22.2 | 92.7 | 10.4 |
| 2.5 | 7.5 | 93.0 | 6.1 | 97.6 | 20.4 |
| 5.0 | 3 | 97.5 | 17.0 | 79.1 | 3.4 |
| 5.0 | 5 | 94.7 | 7.1 | 90.3 | 4.8 |
| 5.0 | 7.5 | 95.3 | 9.1 | 96.8 | 18.4 |
| 5.0 | 10 | 96.7 | 15.0 | 97.4 | 18.5 |
| 10 | 3 | 93.4 | 6.6 | 89.6 | 5.3 |
| 10 | 5 | 94.5 | 7.7 | 89.5 | 7.0 |
| 10 | 7.5 | 90.6 | 7.7 | 93.3 | 7.9 |
| 10 | 10 | 95.1 | 7.0 | 97.0 | 15.9 |

β-Car$^{OX}$ in Combination with Anitcancer Agents

Often, classical anticaner drugs are ineffective because cancerous cells acquire resistance towards the treatment. In many cases, this phenomenon is linked to and increased level of glutathione (GSH), which protects cancerous cells by reacting with the active component of the drug and thereby assisting its removal from the cell. Data given in Table 7 show that β-Car$^{OX}$ is able to substantially lower the level of GSH in the DA-3 mouse mammary cancer cell line, which is the same cell line used in the animal model for assessing antitumor activity. The results in Table 7 compare very favorably with the corresponding effect of buthionine sulfoximine (BSO), a more toxic inhibitor of GSH biosynthesis, which currently is undergoing testing as an anticancer agent.

TABLE 7

Effect of β-Car$^{OX}$ on the Level of
Glutathione in the DA-3 Cell Line.

| β-Car$^{OX}$ (μM) | GSH (nmol/mg protein) |
|---|---|
| 0 | 30 |
| 5 | 38 |
| 10 | 6 |
| 20 | 3 |

Figure 9A:
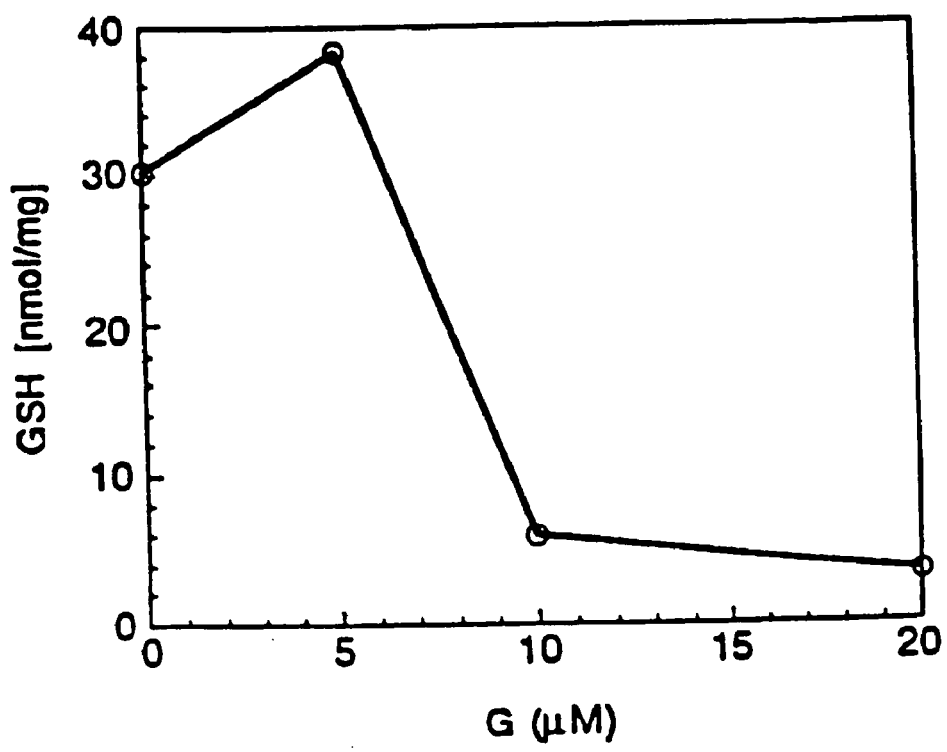
FIG. 9a is a graph illustrating the in vitro effect of oxidized β-carotene on glutathione level in the DA-3 cell line.
Figure 9B:
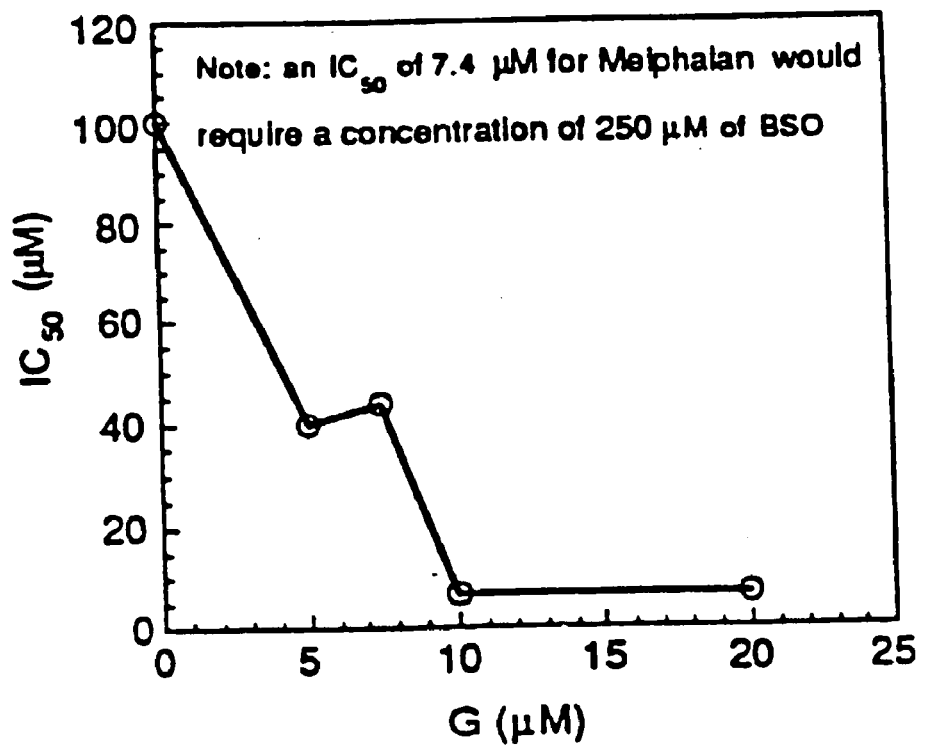
FIG. 9b is a graph illustrating the in vitro effect of β-$Car^{ox}$ on the $IC_{50}$ of melphalan in the DA-3 cell line.
Figure 10:
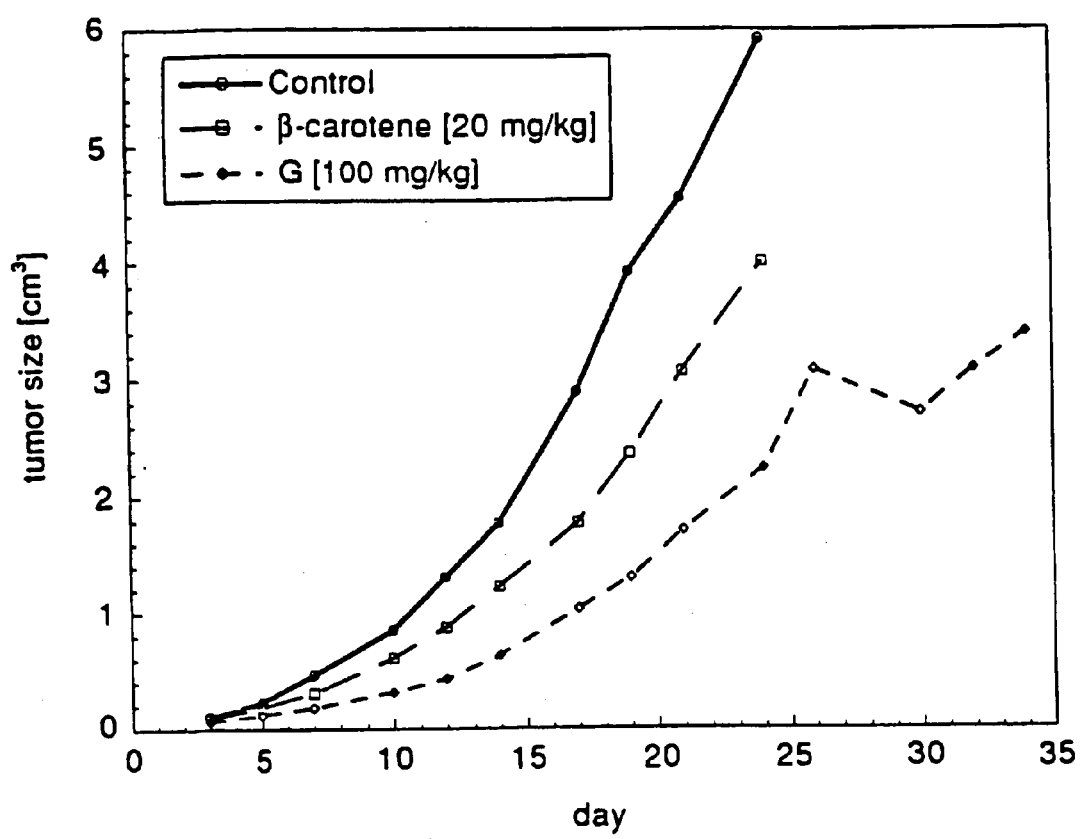
FIG. 10 is a graph showing the antitumor properties of β-carotene and oxidized β-carotene in ovarian cancer.

The benefit of the cellular GSH-lowering effect is illustrated by what happens to the viability of DA-3 cells, using the MTT test, treated with both β-Car$^{OX}$ and melphalan, a classical anticancer agent. The data in Table 8 show that the IC$_{50}$ of melphalan is reduced dramatically in the presence of low concentrations of β-Car$^{OX}$ (see FIGS. 9a and 9b).

This effect suggests that co-administration of β-Car$^{OX}$ with a conventional anticancer agent, such as melphalan, will increase the sensitivity of cancerous cells towards the anticancer drug. This can be helpful in one of two ways: a) the same dose can achieve a higher concentration of the drug in the cancerous cells; b) a lower dose will be required for a therapeutic effect thereby reducing the unwelcome side effects resulting from the high, general toxicity of melphalan.

TABLE 8

Effect of β-Car$^{OX}$ on the IC$_{50}$ of
Melphalan in the DA-3 Cell Line.

| β-Car$^{OX}$ (μM) | IC$_{50}$ Melphalan (μM) |
|---|---|
| 0 | 100 |
| 5 | 40 |
| 7.5 | 44 |
| 10 | 6.6 |
| 20 | 6.8 |

In Vivo Tests

Figure 11A:
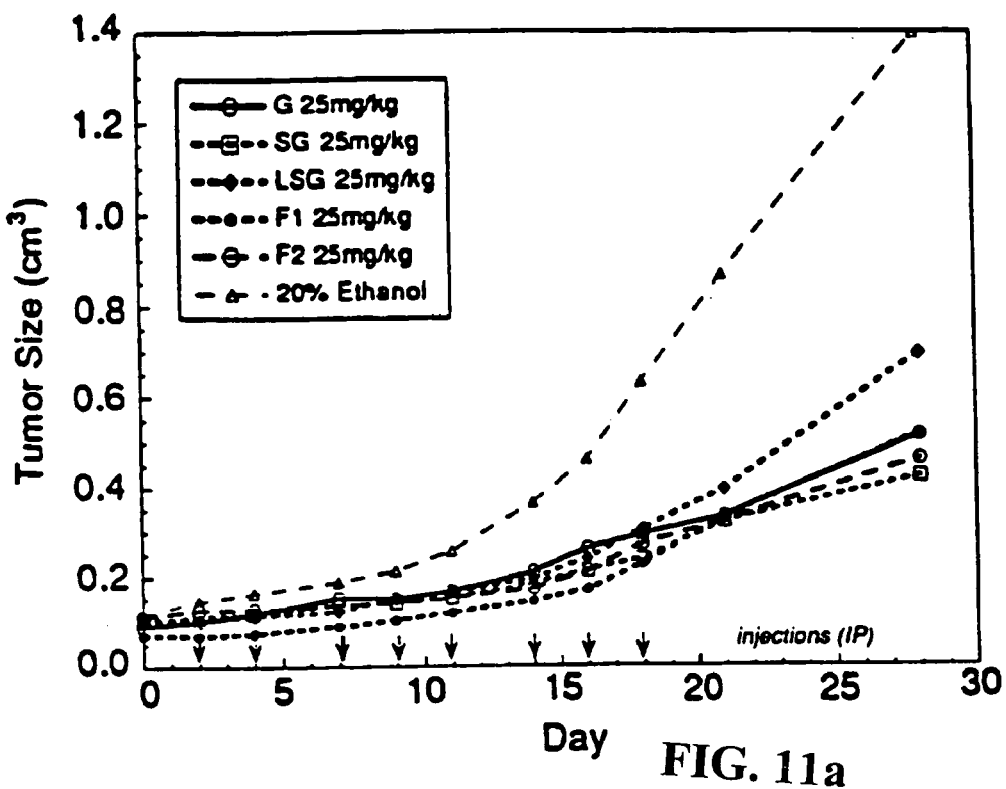
FIGS. 11a and 11b are graphs showing the inhibitory effect of various fractions of the invention on tumor growth in the mouse DA3 model.
Figure 11B:
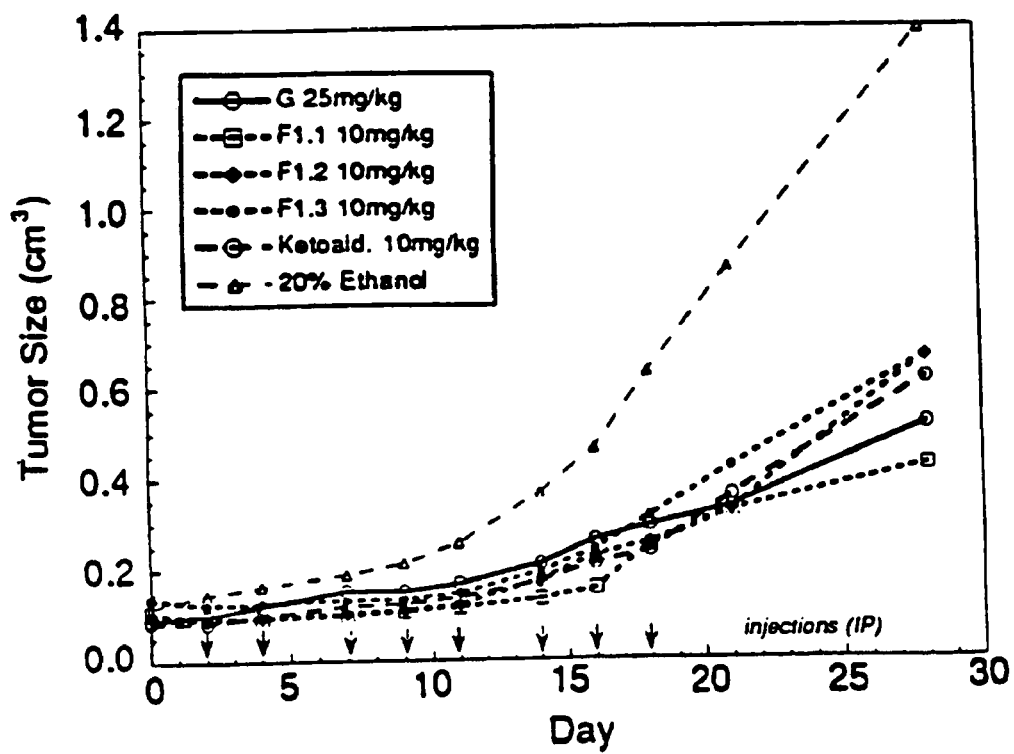

The mouse D1-DMBA-3 (DA-3) mammary adenocarcinoma model was used. The results displayed in FIGS. 11a and 11b show that several fractions were at least as potent (fractions SG. F1, F2) or more potent (fractions F1.1, F1.2, F1.3; taking into account lower concentrations used) than β-Car$^{OX}$.

Table 9 shows the estimated tumor volume expressed relative to the control (i.e., the group receiving the vehicle only) on day 28 of the experiment. In contrast to what was previously observed for β-Car$^{OX}$, it can be seen that at least in the case of fraction F1 a dose-response effect exists.

TABLE 9

In Vivo Antitumor Activity.

| Sample | Dose (mg/kg body) | Relative Tumor Size (28 days) |
|---|---|---|
| 20% ethanol | N/A | (1.00) |
| β-Car$^{OX}$ | 25 | 0.036 |
| SG1 | 25 | 0.30 |
| LSG | 25 | 0.49 |
| F1 | 5 | 0.72 |
| F1 | 10 | 0.49 |
| F1 | 25 | 0.37 |
| F2 | 25 | 0.33 |
| F1.1 | 10 | 0.30 |
| F1.2 | 10 | 0.47 |
| F1.3 | 10 | 0.47 |

An alternative delivery mode was tested on the same model for two fractions, F1 and F2, showing that both fractions when applied orally are at least as effective as when applied intraperitoneally.

2-Methyl-6-Oxo-2,4-Heptadienal

2-Methyl-6-Oxo-2,4-Heptadienal ("the ketoaldehyde") has been identified as a major component of fraction F1.2, described above. In U.S. Ser. No. 08/527,039, hereby incorporated by reference, the ketoaldehyde was shown to have a cytostatic effect on human colon carcinoma (HCT116), human neuroblastoma (IMR32), human acute promyelocytic leukemia (NB4), and human chronic myelogenous leukemia (K562) cell lines. Furthermore, in a mouse DA-3 mammary adenocarcinoma model the ketoaldehyde limited the tumor volume to less than 50% of the control over 28 days.

In vitro and in vivo results demonstrate that the ketoaldehyde has inhibitory activity in cell cultures and tumors derived from cell lines representing a broad range of cancers. The effect of the ketoaldehyde in vivo has been demonstrated using several mouse tumor models, which demonstrate activity against both tumor growth and the formation of metastases. Specifically, inhibition of tumor activity has been demonstrated in mice for three human colorectal cell lines and one human breast cancer cell line, in addition to the mouse breast cancer cell line previously described.

Inhibition of tumor growth and formation of metastases was achieved without any sign of toxicity in the animals. Thus, the ketoaldehyde provides a non-toxic method of controlling the growth and spread of various cancers. Furthermore, the ketoaldehyde can be used in combination with other anticancer agents for the treatment of cancer.

In vitro Tests

The effect of the ketoaldehyde upon the inhibition of cell proliferation in cultured cancer cells was determined using a conventional, fluorescence-based anti-proliferative assay and a flow cytometry method. The extent of apoptosis was determined for some cell lines as well.

Figure 12:
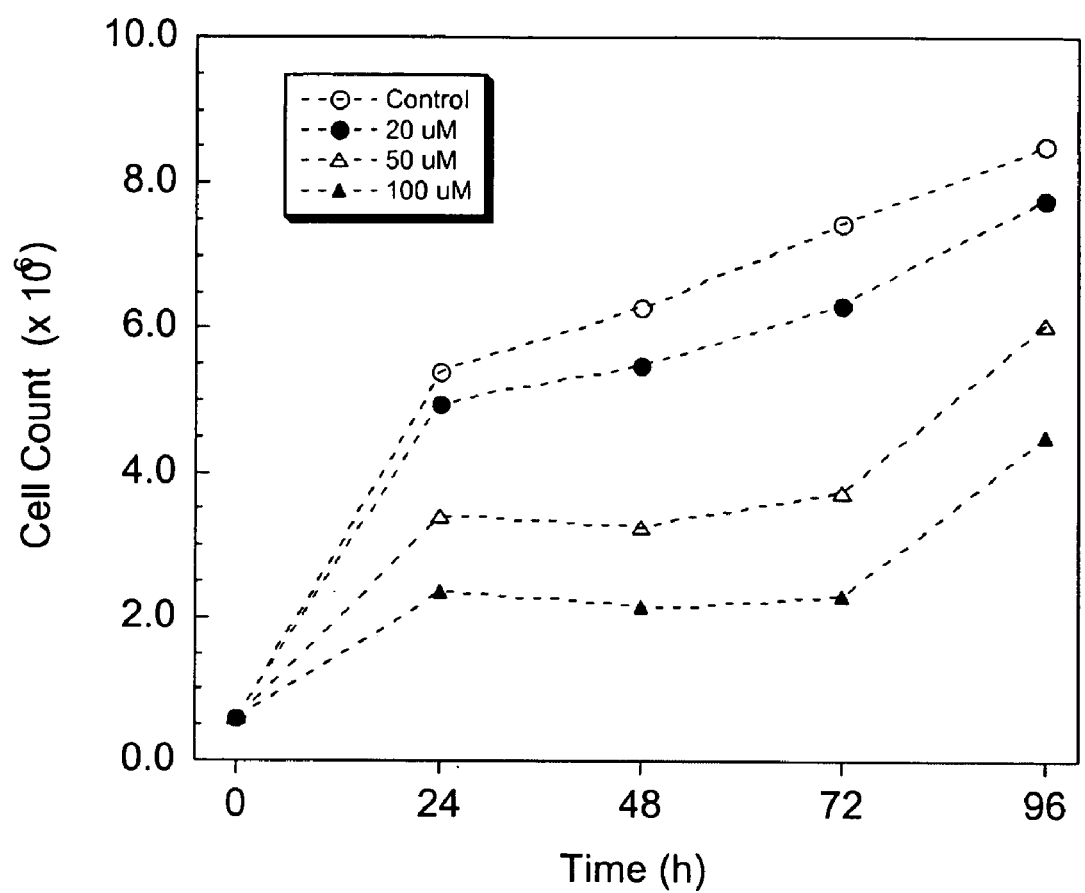
FIG. 12 is a graph illustrating the inhibition of proliferation of SW480 colorectal cancer cell line by 20, 50 and 100 μM ketoaldehyde at 24, 48, 72 and 96 hours.
Figure 13:
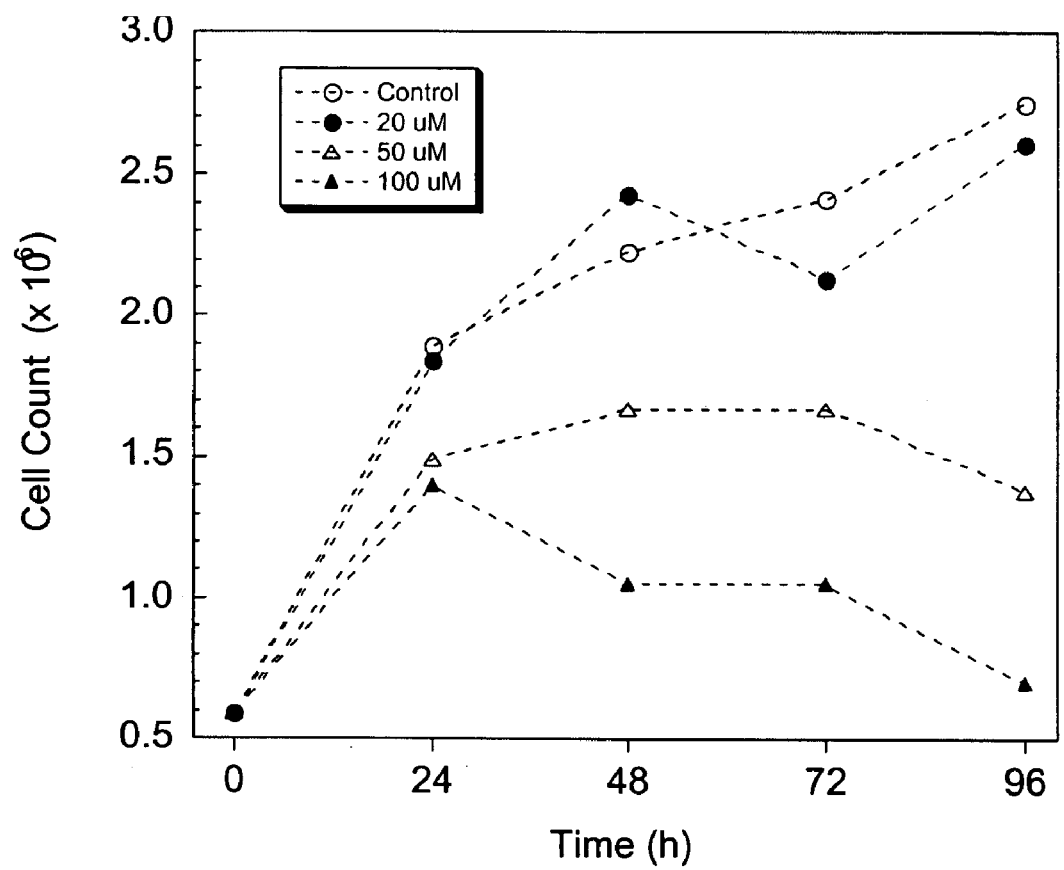
FIG. 13 is a graph illustrating the inhibition of proliferation of MCF-7 breast cancer cell line by 20, 50 and 100 μM ketoaldehyde at 24, 48, 72 and 96 hours.

The effect of different concentrations of the ketoaldehyde upon the proliferation of the SW480 colorectal and MCF-7 breast cancer cell lines as a function of time is provided in FIGS. 12 and 13, respectively. The inhibition of proliferation in individual cell lines is summarized in Table 10, which provides a relative ranking of the ketoaldehyde's IC$_{50}$ for each cell line.

Although the ketoaldehyde exerts control over the growth of cell populations in various cancer lines, it appears that apoptosis is not the primary cause of inhibition of proliferation. This indicates an indirect means of control of cellular proliferation, which is consistent with the lack of toxicity seen in tumor-bearing mice treated with the ketoaldehyde.

TABLE 10

Relative Activity of The ketoaldehyde in Inhibiting the Proliferation of Various Cancer Cell Lines.

| Human Cell Line | Relative Inhibition of Proliferation[1] | Apoptosis |
|---|---|---|
| D 341 medulloblastoma (brain)[2] | +++ | ++ |
| HL-60 acute promyelocytic leukemia[2] | +++ | +++ |
| HCC 1143 breast carcinoma[2] | + | + |
| MCF-7 breast adenocarcinoma[2] | +++ | + |
| SW480 colorectal adenocarcinoma[2] | +++ | ++ |
| NCI-H23 non-small cell lung cancer[2] | +++ | +++ |
| SK-Mel malignant melanoma epidermal[2] | ++ | ++ |
| HT29 colon cancer[3] | ++ | n/a |
| HCT116 colon cancer[3] | +++ | n/a |
| IMR32 neuroblastoma[3] | +++ | n/a |
| NB4 acute promyelocytic leukemia[3] | ++ | n/a |
| K562 chronic myelogenous leukemia[3] | + | n/a |

[1]Relative responses are designated as +++, ++ and + corresponding approximately to $IC_{50}$'s of 50, 100 and >100 µM (micromolar), respectively.
[2]Flow cytometry testing at 20–100 µM the ketoaldehyde for effects on cells at 24, 48, 72 and 96 hours.
[3]Fluorescence-based measurements for 10–175 µM the ketoaldehyde at 72 hours.

In vivo Testing

In both syngeneic and nude mouse models, the ketoaldehyde causes major inhibition of the growth of subcutaneously implanted tumors.

Results obtained for the syngeneic murine breast cancer DA-3 model using 3 groups of 10 mice treated with the ketoaldehyde (10 mg/kg), the oxidized β-carotene mixture (25 mg/kg) and drug vehicle alone, control group, respectively, were described in U.S. Ser. No. 08/527,039 (see FIG. 11b).

Figure 14:
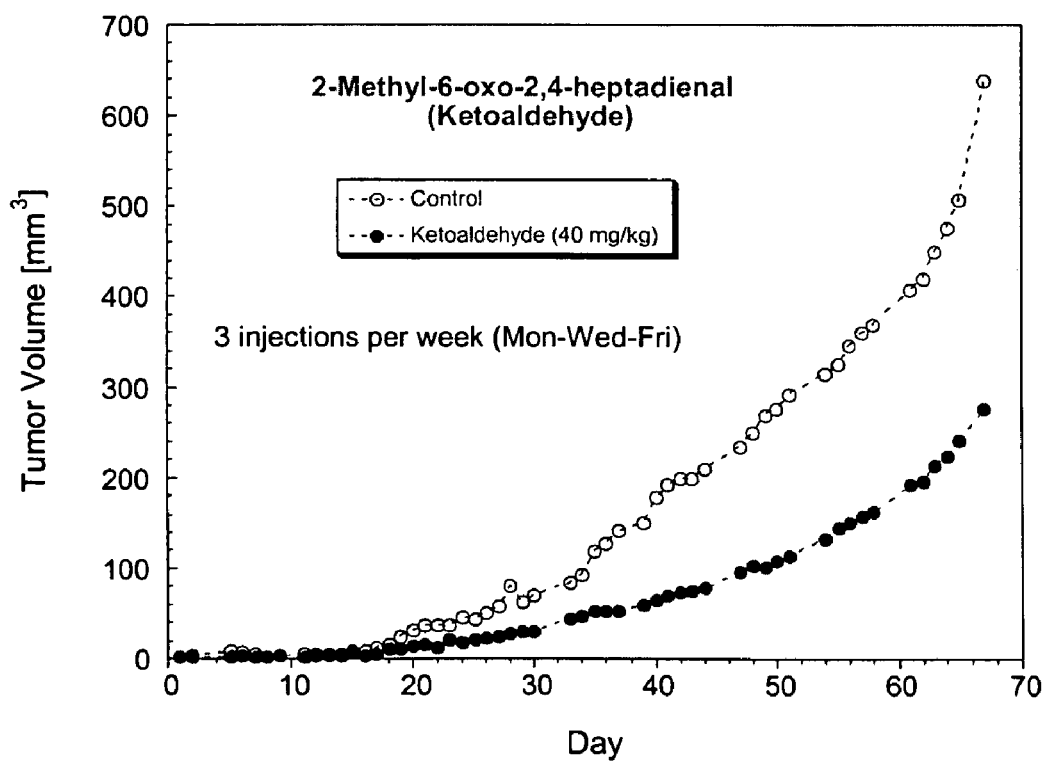
FIG. 14 is a graph illustrating the inhibition of growth by the ketoaldehyde of a tumor derived from human colorectal cancer cells. Balb/c nude mice were inoculated subcutaneously in the flank with $5.0 \times 10^6$ cells of the SW-480 human colorectal adenocarcinoma cell line. There were 7 control animals and 7 animals in the treatment group. The administration schedule was 40 mg/kg of ketoaldehyde in 20% ethanol in saline given by intraperitoneal injection 3 times per week (Monday, Wednesday and Friday).

The ketoaldehyde provides a significant degree of tumor growth control for a period of more than 67 days in a nude mouse xenograft model of human colon cancer (human colon cancer cell line, SW480; see FIG. 14). This result was obtained by administering a modest amount of the ketoaldehyde (40 mg/kg body weight) three times per week (Mon-Wed-Fri), without any optimization of the dosing schedule. Tumors derived from another colorectal cell line, LS174T, grown in severely compromised immuno-deficient (SCID) mice, also have responded well to the same thrice-weekly dosing of the ketoaldehyde.

Tumors derived from the MCF-7 human breast cancer cell line responded to a thrice-weekly dosing regimen of the ketoaldehyde at 40 mg/kg body weight. An improved response was obtained with daily dosing at the same level. While the MCF-7 cell line appears to be less susceptible to the ketoaldehyde than the SW480 cell line, it should be noted that the MCF-7-derived tumors grow more aggressively than those derived from SW480, which necessitated using 20-fold fewer MCF-7 cells to obtain an initially slower rate of tumor growth.

The ketoaldehyde is also active against human LNCaP-FGC-10 prostate tumors grown in nude mice.

The results for the in vivo tumor growth control studies are summarized in Table 11.

TABLE 11

Relative response of various tumors to the ketoaldehyde.

| Tumor model | Cancer Origin | Cell Line | Mouse Type | Weekly Dose[1] | Response[2] |
|---|---|---|---|---|---|
| Murine Syngeneic | Mammary | DA-3 | Balb/c | 3 × 10 mg | +++ |
| Human Xenograft | Colorectal | SW480 | Nude | 3 × 40 mg | +++ |
| | Colorectal | HT29 | Nude | 3 × 25 mg | ++ |
| | Colorectal | LS174T | SCID | 3 × 40 mg | ++ |
| | Breast | MCF-7 | Nude | 7 × 40 mg | ++ |
| | Prostate | LNCaP-FGC-10 | Nude | 3 × 40 mg | + |

[1]Dose expressed in mg/kg body weight and given by intraperitoneal injection of the ketoaldehyde in 20% aqueous ethanol in saline either 3 times per week (Mon, Wed, Fri) or daily.
[2]Qualitative ranking. The response is affecting not only by the inherent sensitivity of the cell line to the drug compound, but also by the native rate of growth of the tumor in the host animal and the pharmacokinetics of the drug, neither of which were optimized to obtain maximal growth inhibitory benefit of the ketoaldehyde.

Toxicity

No toxicity was observed for the ketoaldehyde at therapeutically functional doses (the dosing levels required for inhibition of tumor growth or metastases). A pilot toxicity study suggests that the $LD_{100}$ of the ketoaldehyde in mice is approximately 400 mg/kg body weight. Significant inhibition of tumor growth has been obtained with doses of only 10–40 mg/kg body weight. Thus, the ketoaldehyde has a therapeutic index (400/(10–40)) of approximately 10 to 40.

Inhibition of Metastases

Anti-metastatic activity has been demonstrated in a model that measures the spread into the lung of lung cancer cells originating from a subcutaneously implanted tumor (see Table 12).

The well-known Lewis lung carcinoma model was used as follows: cells were injected subcutaneously into the flanks of C57 BL/6 mice, which were assigned into control and treated groups containing ten animals per group. On day 8, the tumor was excised. The ketoaldehyde (200 mg/kg body weight) in 20% aqueous ethanol or drug vehicle (aqueous ethanol) was administered intraperitoneally on days 9, 11, 13, 15 and 19. On day 22, the animals were sacrificed and their lungs were removed. The lungs were weighed and the number of metastases determined by counting the nodules established in each lung.

Results: there was a highly significant reduction of almost 50% in the number of lung metastases in the treated animals, which corresponded to a significantly lower mass of lung tissue (Table 12).

TABLE 12

Effect of the ketoaldehyde on metastases in mouse lung

| | Mean Lung Weight ± SEM | Mean No. Metastases ± SEM |
|---|---|---|
| Control | 0.287 ± 0.013 g | 28.0 ± 2.4 |
| Treated | 0.229 ± 0.012 g | 14.4 ± 4.1 |

TABLE 12-continued

Effect of the ketoaldehyde on metastases in mouse lung

|  | Mean Lung Weight ± SEM | Mean No. Metastases ± SEM |
| --- | --- | --- |
| Difference | 0.058 g | 13.6 |
| Significance, 2-tail t-test | 0.004 | 0.01 |

Combination Therapy

The ketoaldehyde can be used in combination with another anticancer agent for the treatment of cancer and/or inhibiting the formation of metastases. Anticancer agents to be used in combination with the ketoaldehyde include, without limitation, those agents provided in Table 13.

Desirably, the ketoaldehyde is added to an existing clinical regimen (e.g., paclitaxel for the treatment of breast cancer) for the purpose of reducing the minimum efficacious dose. The benefit to the patient is an increase in the therapeutic index of the anticancer agent when used in combination with the ketoaldehyde. Accordingly, the ketoaldehyde can be added to any existing cancer therapy regimen for the purpose of reducing adverse drug reactions, extending the life of the patient, and/or improving the cure rate.

TABLE 13

Chemotherapeutic Agents

| Class | Type of Agent | Nonproprietary Names | Cancers |
| --- | --- | --- | --- |
| Alkylating agents | Nitrogen mustards | mechlorethamine | Hodgkin's disease, non-Hodgkin's lymphomas |
|  |  | Cyclophosphamide Ifosfamide | Acute and chronic lymphocytic, leukemias, Hodgkin's disease, non-Hodgkin's lymphomas, multiple myeloma,neuroblastoma, breast, ovary, lung, Wilms' tumor, cervix, testis, soft-tissue sarcomas |
|  |  | Melphalan | Multiple myeloma, breast, ovary |
|  |  | Chlorambucil | Chronic lymphocytic leukemia, Primary macroglobulinemia, Hodgkin's disease, non-Hodgkin's lymphomas |
|  |  | Uracil mustard | Leukemia |
|  |  | Estramustine | Solid Tumors |
|  | Ethylenimines and Methylmelamines | Mitomycin C | Colorectal, ocular |
|  |  | AZQ | Primary brain tumors |
|  |  | Thiotepa | Bladder, breast, ovary |
|  | Alkyl Sulfonates | Busulfan Hepsulfam | Chronic myelogenous leukemia |
|  | Nitrosoureas | Carmustine | Hodgkin's disease, non-Hodgkin's lymphomas, primary brain tumors, multiple myeloma, malignant melanoma |
|  |  | Lomustine | Hodgkin's disease, non-Hodgkin's lymphomas, primary brain tumors, small-cell lung |
|  |  | Semustine | Primary brain tumors, stomach, colon |
|  |  | Streptozocin | Malignant pancreatic insulinama, malignant carcinoid |
|  | Triazines | Dacarbazine | Malignant melanoma, Hodgkin's disease, soft-tissue sarcomas |
|  | Platinum Complexes | Cisplatin Carboplatin | Testis, ovary, bladder, head and neck, lung, thyroid, cervix, endometrium, neuroblastoma, osteogenic sarcoma |
|  | Methyl Hydrazine Derivative | Procarbazine | Hodgkin's disease |
| Antimetabolites | Folic Acid Antagonists | Methotrexate Trimetrexate | Acute lymphocytic leukemia, choriocarcinoma, mycosis fungoides, breast, head and neck, lung, osteogenic sarcoma |
|  | Pyrimidine Antagonists | Fluouracil Floxuridine | Breast, colon, stomach, pancreas, ovary, head and neck, urinary bladder, skin, adenocarcinomas |
|  |  | Cytarabine | Acute myelogenous and acute lymphocytic leukemias |
|  |  | Fludarabine Phosphate | Lymphoproliferative disease |
|  |  | Capecitabine | Breast, renal cell, prostate |
|  |  | Azacitidine | acute leukemias |

TABLE 13-continued

Chemotherapeutic Agents

| Class | Type of Agent | Nonproprietary Names | Cancers |
|---|---|---|---|
| | Purine Antagonists | Thioguanine | Acute myelogenous, acute lymphocytic and chronic myelogenous leukemias |
| | | Mercaptopurine | Acute lymphocytic, acute myelogenous and chronic myelogenous leukemias |
| | | Allopurine | leukemias |
| | | Cladribine | Hairy cell leukemia |
| | | Gemcitabine | Pancreatic, soft tissue carcinomas |
| | | Pentostatin | Hairy cell leukemia, mycosis fungoides; chronic lymphocytic leukemia |
| Antimitotic Agents | | Vinblastine | Hodgkin's disease, non-Hodgkin's lymphomas, breast, testis |
| | | Vincristine | Acute lymphocytic leukemia, neuroblastoma, Wilms' tumor, rhabdomyosarcoma, Hodgkin's disease, non-Hodgkin's lymphomas, small-cell lung |
| DNA Topoisomerase II Ihibitors | | Etoposide | Testis, small-cell lung, oat-cell lung, breast, Hodgkin's disease, non-Hodgkin's lymphomas, acute myelogenous leukemia, Kaposi's sarcoma |
| | | Teniposide | |
| DNA Topoisomerase I Ihibitors | | Topotecan | Ovarian, colorectal |
| | | Irinotecan | |
| | | Camptothecin | |
| | | 9-Aminocamptothecin | |
| Taxanes | | Paclitaxel | Breast |
| | | Docetaxel | |
| DNA Intercalators | | Daunorubicin | Acute myelogenous and acute lymphocytic leukemias |
| | | Doxorubicin | Ewing's sarcoma, osteosarcoma, rhabdomyosarcomas, Hodgkin's disease, non-Hodgkin's lymphomas, acute leukemias, multiple myeloma, breast, genitourinary, thyroid, lung, ovarian, endometrial, testicular, stomach, neuroblastoma |
| | | Dactinomycin | Choriocarcinoma, Wilms' tumor, rhabdomyosarcoma, testis, Kaposi's sarcoma |
| | | Idarubincin | Acute myeloid leukemia |
| | | Plicamycin | Testicular cancer |
| | | Mitomycin | Squamous sell carcinomas, small bladder papillomas, adenocarcinomas, pancreas, lung, colon, stomach, cervix, breast, head and neck |
| | | Amsacrine | Acute myelogenous leukemia, ovarian cancer, lymphomas |
| | | Bleomycin | Testicular, head and neck, skin, esophagus, squamous cell, colorectal, lung, genitourinary tract, cervix, ovarian, breast, Hodgkin's disease, non-Hodgkin's lymphomas |
| Hormonal Agents | Aromatase Inhibitors | Aminoglutethimide | Breast |
| | | Anastrozole | |

TABLE 13-continued

Chemotherapeutic Agents

| Class | Type of Agent | Nonproprietary Names | Cancers |
|---|---|---|---|
| | 5-alpha-Reductase Inhibitors | Finasteride Ketoconazole | Prostate |
| | Estrogen and Androgen Inhibitors | Tamoxifen Flutamide | Breast Prostate |
| | Gonadotropin Releasing Hormone Agonists | Leuprolide Goserelin | Prostate |
| Tyrosine Kinase Inhibitors | ABL Inhibitors | Gleevec ™ (Novartis) | chronic myelogenous leukemia or acute lymphoblastic leukemia |
| | PDGFR Inhibitors | Leflunomide (Pharmacia), SU5416 (Pharmacia), SU6668 (Pharmacia), PTK787 (Novartis) | gastrointestinal stromal tumor, small cell lung cancer, glioblastoma multiforme, and prostate cancer |
| | EGFR Inhibitors | Iressa ™ (AstraZeneca), Tarceva ™, (Oncogene Science), trastuzumab (Genentech), Erbitux ™ (ImClone), PK1166 (Novartis), GW2016 (GlaxoSmithKline), EKB-509 (Wyeth), EKB-569 (Wyeth), MDX-H210 (Medarex), 2C4 (Genentech), MDX-447 (Medarex), ABX-EGF (Abgenix), CI-1033 (Pfizer) | non-small-cell lung cancer, breast cancer, ovarian cancer, bladder cancer, prostate cancer, salivary gland cancer, pancreatic cancer, endometrial cancer, colorectal cancer, kidney cancer, head and neck cancer, glioblastoma multiforme |
| | VEGFR Inhibitors | Avastin ™ (Genentech), IMC-1C11 (ImClone), ZD4190 (AstraZeneca), ZD6474 (AstraZeneca) | any solid tumor |
| | Trk Inhibitors | CEP-701 (Cephalon), CEP-751 (Cephalon) | prostate cancer, pancreatic cancer |
| | Flt-3 Inhibitors | MLN518 (Millenium), PKC412 (Novartis) | acute myeloid leukemia |
| Retinoic Acid Derivatives | | 13-cis-retinoic acid, isotretinoin, retinyl palmitate, 4-(hydroxycarbophenyl) retinamide | Acute promyelocytic leukemia, head and neck squamous cell carcinoma |
| Hypoxia-Selective Cytoxins | | Misonidazole Nitracrine | Head and neck Breast |
| Miscellaneous Agents | | Mitoxantrone | Acute acute myelogenous leukemia non-Hodgkin's lymphoma's, breast |
| | | Hydroxyurea | Chronic myelogenous leukemia, polycythemia vera, essental thrombocytosis, malignant melanoma |
| | | L-Asparaginase | Acute lymphocytic leukemia |
| | | Interferon alfa | Hairy cell leukemia., Kaposi's sarcoma, melanoma, carcinoid, renal cell, ovary, bladder, non-Hodgkin's lymphomas, mycosis fungoides, multiple myeloma, chronic myelogenous leukemia |
| | | Rapamycin, CCI-779 | Glioblastoma Multiforme, renal cell carcinoma |
| | | Mitotane | Adrenal carcinoma |

In the methods of the present invention, the dosage and frequency of administration of the ketoaldehyde and additional anticancer agent(s) can be controlled independently. For example, one compound may be administered orally three times per day, while the second compound may be administered intravenously once per day. The compounds may also be formulated together such that one administration delivers both compounds.

The exemplary dosage of the ketoaldehyde and additional anticancer agent(s) to be administered will depend on such variables as the type and extent of the disorder, the overall health status of the patient, the therapeutic index of the selected anticancer agent(s), and their route of administration. Standard clinical trials may be used to optimize the dose and dosing frequency for any particular combination of the invention.

Synthesis of 2-Methyl-6-Oxo-2,4-Heptadienal

The preparation of the ketoaldehyde from the oxidation of β-carotene is an inefficient method of obtaining this compound. The following five-step synthetic pathway describes a convenient preparation of the ketoaldehyde.

First, a compound of formula I is condensed with propionaldehyde in the presence of dimethylamine and propionic acid. The condensation, followed by in situ dehydration under the reaction conditions, leads to a compound of formula II (see reaction 1).

Reaction 1

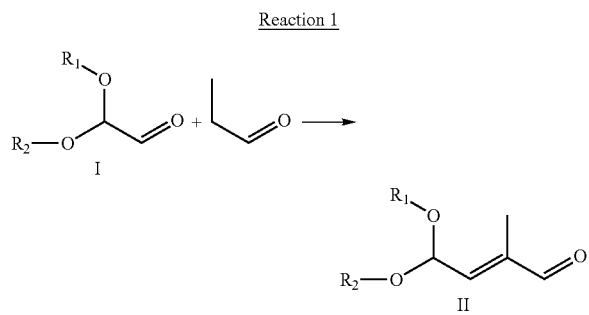

In formulas I and II, $R_1$ and $R_2$ are each, independently, an alkyl of 1 to 8 carbon atoms, a heteroalkyl of 2–8 atoms, an alkene of 2–8 carbon atoms, an alkyne of 2–8 carbon atoms, or an aromatic residue. Optionally, $R_1$ and $R_2$ combine to form a cyclic acetal.

Second, the protection pattern on the aldehyde groups is reversed. This approach necessitates the use of a protective group with reactivity different from that of the existing acetal, such as condensation with a hydroxylamine, as shown in reaction 2, to produce a compound of formula III. Oxime or oxime ether moieties fulfill this requirement and both have been used successfully. Other relatively stable aldehyde protecting groups, such as hydrazones, can also be used. Ideally, the protection should be carried out under conditions where the original acetal function is not disturbed.

Reaction 2

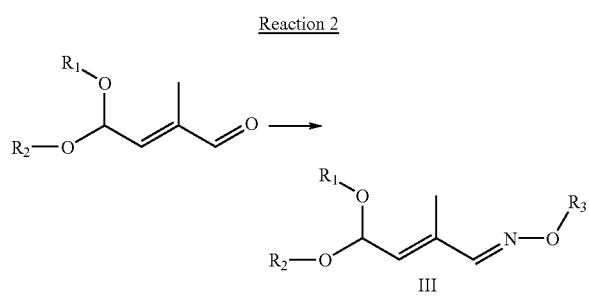

In formula III, $R_1$ and $R_2$ are as described above and $R_3$ is a hydrogen atom, an alkyl of 1 to 8 carbon atoms, a heteroalkyl of 2–8 atoms, an alkene of 2–8 carbon atoms, an alkyne of 2–8 carbon atoms, or an aromatic residue. When $R_3$ is —H, intermediate III is an oxime obtained by reacting the acetal aldehyde III with hydroxylamine. Similarly, oxime ether derivatives of formula III ($R_3$=Me, Et, etc) can be obtained using free alkoxyamine or its salt in the presence of a base. Instead of using alkoxyamine or its salt, it is possible to convert the oxime ($R_3$=H) to an ether ($R_3$=alkyl, heteroalkyl, alkene, alkyne, or aromatic residue) with the use of a proper alkylating agent, for example methyl iodide or dimethyl sulfate.

Third, the acetal group in the compound of formula III can now be selectively cleaved to produce a compound of formula IV, as shown in reaction 3.

Reaction 3

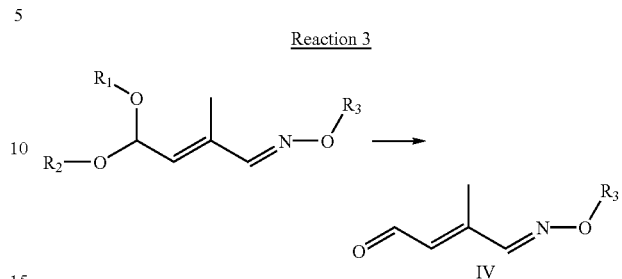

In formula III, $R_3$ is as described above. This deprotection can be carried out, for example, under acidic conditions with the use of Amberlyst™ 15 in acetone containing a sufficient amount of water.

Fourth, condensation with acetone (or its equivalent) can be carried out to obtain the ketooxime of formula V, as shown in reaction 4.

Reaction 4

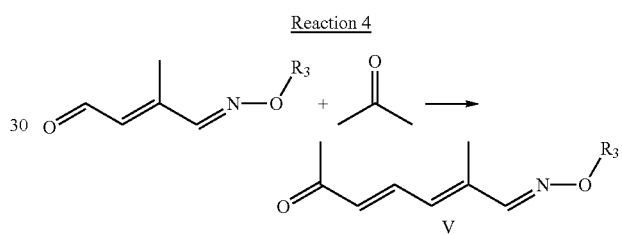

In formula V, $R_3$ is as described above. This reaction can be accomplished using a variety of conditions, for example, an aldol condensation using aqueous NaOH as a base and acetone as both solvent and reagent. The aldol condensation also can be run in methanol, using sodium methoxide as a base and acetone as a reagent.

If the simplest oxime form of formula V ($R_3$=H) is used, it is advantageous to use more that one molar equivalent of the base, for example, 1.1 to 1.5 in order to shorten the reaction time. If the oxime ether form of formula V ($R_3$=alkyl, heteroalkyl, alkene, alkyne, or aromatic residue) is used instead, less then 1 molar equivalent of base, for example 0.1 to 0.5 is sufficient. Alternatively, a Wittig reaction using (2-oxo-propyl)-phosphonic acid dimethyl ester (serving as an equivalent of acetone) can be carried out with alkaline carbonate (such as potassium carbonate) in a protic solvent (such as methanol) or other suitable base/solvent pair to give the intermediate V.

Fifth, the ketooxime of formula V is cleaved to produce the ketoaldehyde. This reaction can be carried out using an acidic catalysis (sulfuric acid), for example, with an excess of aqueous formaldehyde added as an oxime scavenger.

Specific examples are provided below.

Preparation of 4,4-Dimethoxy-2-methyl-but-2-enal

Propionic acid (24.7 mL) was added carefully to an aqueous solution of dimethylamine (40%, 41.6 mL), stirring and cooling (ice-water bath) to ensure the temperature of the mixture did not exceed 10° C. A pale yellow solution formed and the cooling bath was replaced with a heating mantle. From this point on, the temperature was controlled by a digital controller; a temperature probe was placed in the flask and the mantle was connected to the controller. The mixture was warmed to 40° C., the solution became colorless and dimethoxyacetaldehyde (aq. 60%, 100 mL) was added. The mixture was heated to 60° C. and propionaldehyde (42.26 g) was added dropwise at such a rate that the temperature did not exceed 68° C. (ca. 30 min). During the addition the color of the mixture changed, first from yellow to orange, and then to brown. The mixture was vigorously stirred and the temperature was maintained at 70° C. for 24 hours. The reaction mixture was allowed to cool down to a room temperature and then was extracted three times with dichloromethane (100 mL). The combined dichloromethane extracts were washed with water (150 mL). The organic layer was dried over anhydrous sodium sulfate (3 g) and the solvents were evaporated on a rotary evaporator at the room temperature. 117 g of a dark reddish-brown material was obtained. The crude product was distilled under reduced pressure (<0.5 mm Hg) using a modified version of a falling film apparatus at 78° C. (the b.p. of ethyl acetate, which was used as the heating medium). The clear distillate (of formula II, $R_1$ and $R_2$ are methyl; 101 g) was collected in a trap cooled in a dry ice bath.

Preparation of 4,4-dimethoxy-2-methyl-but-2-enal Oxime 4,4-Dimethoxy-2-methyl-but-2-enal (50 g) was placed in a flask and an aqueous solution of ammonium hydroxide (50%, 100 mL) was added dropwise with cooling (ice bath) so that the temperature of the mixture did not exceed 10° C. When the addition was completed, the bath was removed and the reaction was stirred at the room temperature for 2 hours. The resulting mixture was extracted twice with dichloromethane (100 mL). The combined organic layers were washed with distilled water (100 mL). The product (of formula III, $R_1$ and $R_2$ are methyl, $R_3$ is hydrogen; 49.7 g), was obtained as a viscous liquid after removal of the solvent on a rotary evaporator.

Preparation of 2-methyl-but-2-enedial-1-oxime 4,4-Dimethoxy-2-methyl-but-2-enal oxime (65 g) was dissolved in acetone (350 mL) containing water (15 mL). The solution was cooled to 0° C. and Amberlyst™ 15 (98 g) was added. The reaction mixture was stirred for 2 hrs while the temperature was maintained at 0° C. The acidic resin was filtered off, washed with acetone (50 mL) and the combined solutions were evaporated under reduced pressure to yield the product (of formula IV, $R_3$ is hydrogen; 43 g).

Preparation of 2-methyl-but-2-enedial-1-O-methyl-oxime

2-Methyl-but-2-enedial-1-oxime (0.5 g) was dissolved in acetone (15 mL) and methyl iodide (3.14 g) was added, followed by anhydrous potassium carbonate (1.2 g). The reaction mixture was stirred for 3 hrs, the solids were filtered off and the filtrate was evaporated to give the methyl ether (of formula IV, $R_3$ is methyl; 0.51 g).

Preparation of 2-methyl-6-oxo-hepta-2,4-dienal Oxime

An aqueous solution of sodium hydroxide (10%, 21.1 mL) was added slowly to a solution of 2-methyl-but-2-enedial-1-O-methyl-oxime (5 g) in acetone (100 mL) at 0° C. After 2 hrs the mixture was neutralized with a saturated solution of ammonium chloride, extracted with ethyl acetate (3×80 mL), washed with water (100 mL), dried with anhydrous magnesium sulfate and the solvent was evaporated yielding a yellow-orange solid (of formula V, $R_3$ is methyl; 5.1 g).

Preparation of 2-methyl-6-oxo-hepta-2,4-dienal

Concentrated sulfuric acid (0.9 mL) was added slowly at ambient temperature with stirring to a suspension of 2-methyl-6-oxo-hepta-2,4-dienal oxime (0.5 g) in a mixture of aqueous formaldehyde (5 mL, 37%) and water (5 mL). A clear solution formed and after 30 minutes the product was extracted with dichloromethane (3×20 mL) and washed with saturated sodium bicarbonate and water. The solution was dried with anhydrous magnesium sulfate and the solvent was evaporated to give the ketoaldehyde as a yellow solid (0.42 g).

Pharmaceutical Compositions

The invention features methods of treating cancer by administering the ketoaldehyde in combination with one or more additional anticancer agents. These may be formulated together or separately and administered to patients with a pharmaceutically acceptable diluent, carrier, or excipient, in unit dosage form. Administration may be topical, parenteral, intravenous, intra-arterial, subcutaneous, intramuscular, intracranial, intraorbital, ophthalmic, intraventricular, intracapsular, intraspinal, intracisternal, intraperitoneal, intranasal, aerosol, by suppositories, or oral administration.

Therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in "Remington: The Science and Practice of Pharmacy" (20th ed., ed. A. R. Gennaro AR., 2000, Lippincott Williams & Wilkins). Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the ketoaldehyde and/or anticancer agent. Nanoparticulate formulations (e.g., biodegradable nanoparticles, solid lipid nanoparticles, liposomes) may be used to control the biodistribution of the ketoaldehyde and/or anticancer agent. Other potentially useful parenteral delivery systems include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycholate and deoxycholate, or may be oily solutions for administration in the form of nasal drops, or as a gel. The concentration of the ketoaldehyde and anticancer agent(s) in the formulation will vary depending upon a number of factors, including the dosage of the drug to be administered and the route of administration.

The ketoaldehyde and/or anticancer agent(s) may be optionally administered as a pharmaceutically acceptable salt, such as a non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include zinc, iron, and the like. Optionally, the ketoaldehyde is formulated as the sodium salt of the bisulfite adduct.

Administration of either the ketoaldehyde or anticancer agent(s) in controlled release formulations is useful where the ketoaldehyde and/or anticancer agent(s) has (i) a narrow therapeutic index (e.g., the difference between the plasma concentration leading to harmful side effects or toxic reactions and the plasma concentration leading to a therapeutic effect is small; generally, the therapeutic index, TI, is defined as the ratio of median lethal dose ($LD_{50}$) to median effective dose ($ED_{50}$)); (ii) a narrow absorption window in the gastrointestinal tract; or (iii) a short biological half-life, so that frequent dosing during a day is required in order to sustain the plasma level at a therapeutic level.

Many strategies can be pursued to obtain controlled release in which the rate of release outweighs the rate of metabolism of the ketoaldehyde and/or anticancer agent(s). For example, controlled release can be obtained by the appropriate selection of formulation parameters and ingredients, including, e.g., appropriate controlled release compositions and coatings. Examples include single or multiple unit tablet or capsule compositions, oil solutions, suspensions, emulsions, microcapsules, microspheres, nanoparticles, patches, and liposomes.

Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and antiadhesives (e.g., magnesium stearate, zinc stearate, stearic acid, silicas, hydrogenated vegetable oils, or talc).

Formulations for oral use may also be provided as chewable tablets, or as hard gelatin capsules wherein the active ingredient is mixed with an inert solid diluent, or as soft gelatin capsules wherein the active ingredient is mixed with water or an oil medium.

OTHER EMBODIMENT

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in molecular biology or related fields are intended to be within the scope of the invention.

What is claimed is:

1. A pharmaceutical composition comprising 2-methyl-6-oxo -2,4-heptadienal, wherein said composition is formulated as a tablet or capsule and wherein β-carotene and oxidation products of β-carotene other than 2-methyl-6-oxo-2,4-heptadienal are less than 10% of the mass of 2-methyl-6-oxo-2,4-heptadienal in said composition.

2. The pharmaceutical composition of claim 1, wherein β-carotene and oxidation products of β-carotene other than 2-methyl-6-oxo-2,4-heptadienal are less than 1% of the mass of 2-methyl-6-oxo-2,4-heptadienal in said composition.

3. The pharmaceutical composition of claim 2, further comprising an anticancer agent selected from mechlorethamine, cyclophosphamide, ifosfamide, melphalan, chlorambucil, uracil mustard, estramustine , mitomycin C, AZQ, thiotepa, busulfan, hepsulfam, carmustine, lomustine, semustine, streptozocin, dacarbazine, cisplatin, carboplatin, procarbazine, methotrexate, trimetrexate, fluouracil, floxu- ridine, cytarabine, fludarabine phosphate, azacitidine, thioguanine, mercaptopurine, cladribine, allopurine, gemcitabine, pentostatin, vinbiastine, vincristine, etoposide, teniposide, topotecan, irinotecan, camptothecin, 9-aminocamptothecin, paclitaxel, docetaxel, daunorubicin, doxorubicin, dactinomycin, idarubincin, plicamycin, mitomycin, amsacrine, bleomycin, aminoglutethimide, anastrozole, finasteride, ketoconazole, tamoxifen, flutamide, leuprolide, goserelin, imatinib mesylate, Leflunomide, SU5416, SU6668, PTK787, gefitinib , erlotinib hydrochloride , trastuzumab, cetuximab , PKI166, GW2016, EKB-509, EKB -569, MDX-H210, 2C4, MDX-447, ABX-EGF, CI-1033, bevacizumab, IMC-1C11, ZD4190, ZD6474, CEP-701, CEP-751, MLN518, PKC412, 13-cis-retinoic acid, isotretinoin, retinyl palmitate, 4-(hydroxycarbophenyl) retinamide, misonidazole, nitracrine, mitotoxantrone, hydroxyurea, 1-asparginase, interferon alfa, rapamycin, CCI-779, and mitotane.

4. A pharmaceutical pack comprising 2-methyl-6-oxo-2, 4-heptadienal and an anticancer agent selected from mechiorethamine, cyclophosphamide, ifosfamide, meiphalan, chiorambucil, uracil mustard, estramustine , mitomycin C, AZQ, thiotepa, busulfan, hepsulfam, carmustine, lomustine, semustine, streptozocin, dacarbazine, cisplatin, carboplatin, procarbazine, methotrexate, trimetrexate, fluouracil, floxuridine, cytarabine, fludarabine phosphate, azacitidine, thioguanine, mercaptopurine, cladribine, allopurine, gemcitabine, pentostatin, vinbiastine, vincristine, etoposide, teniposide, topotecan, irinotecan, camptothecin, 9-aminocamptothecin, paclitaxel, docetaxel, daunorubicin, doxorubicin, dactinomycin, idarubincin, plicamycin, mitomycin, amsacrine, bleomycin, aminoglutethimide, anastrozole, finasteride, ketoconazole, tamoxifen, flutamide, leuprolide, goserelin, imatinib mesylate, Leflunomide, SU5416, SU6668, PTK787, gefitinib, erlotinib hydrochloride, trastuzumab, cetuximab, PKI166, GW2016, EKB-509, EKB-569, MDX-H210, 2C4, MDX-447, ABX-EGF, CI-1033, bevacizumab, IMC-1C11, ZD4190, ZD6474, CEP-701, CEP-751, MLN518, PKC412, 13-cis-retinoic acid, isotretinoin, retinyl palmitate, 4-(hydroxycarbophenyl) retinamide, misonidazole, nitracrine, mitotoxantrone, hydroxyurea, 1-asparginase, interferon alfa, rapamycin, CCI-779, and mitotane, wherein β-carotene and oxidation products of β-carotene other than 2-methyl -6-oxo-2,4-heptadienal are less than 10% of the mass of 2-methyl-6-oxo-2,4-heptadienal in said pharmaceutical pack.

5. The pharmaceutical pack of claim 4, wherein said 2-methyl -6-oxo-2,4-heptadienal and said anticancer agent inhibitor are formulated separately and in individual dosage amounts.

6. A pharmaceutical composition comprising 2-methyl-6-oxo -2,4-heptadienal, wherein said composition is formulated as a powder, nasal drop, or aerosol and wherein β-carotene and oxidation products of β-carotene other than 2-methyl-6-oxo-2,4-heptadienal are less than 10% of the mass of 2-methyl-6-oxo-2,4-heptadienal in said composition.

7. A pharmaceutical composition comprising 2-methyl-6-oxo -2,4-heptadienal, wherein said composition is formulated for the controlled release of said 2-methyl-6-oxo-2,4-heptadienal and wherein β-carotene and oxidation products of β-carotene other than 2-methyl-6-oxo-2,4-heptadienal are less than 10% of the mass of 2-methyl -6-oxo-2,4-heptadienal in said composition.

8. A pharmaceutical composition comprising 2-methyl-6-oxo oxo-2,4-heptadienal, wherein said composition is formulated as a biodegradable nanoparticle, solid lipid nanoparticle, liposome, microsphere, suspension, or emulsion and wherein β-carotene and oxidation products of β-carotene other than 2-methyl-6-oxo-2,4-heptadienal are less than 10% of the mass of 2-methyl-6-oxo-2,4-heptadienal in said composition.

9. A pharmaceutical composition comprising 2-methyl-6-oxo-2,4-heptadienal and an excipient selected from magnesium stearate, zinc stearate, stearic acid, hydrogenated vegetable oil, hydrogenated naphthalene, talc, silica, lactose, polyoxyethylene-9-lauryl ether, deoxycholate, polyethylene glycol, sucrose, sorbitol, lactide polymer, lactide/glycolide copolymer, ethylene-vinyl acetate copolymer, and polyoxyethylene-polyoxypropylene copolymer, wherein β-carotene and oxidation products of β-carotene other than 2-methyl-6-oxo-2,4-heptadienal are less than 10% of the mass of 2-methyl-6-oxo-2,4-heptadienal in said composition.

10. The pharmaceutical composition of any of claims 6–9, wherein β-carotene and oxidation products of β-carotene other than 2-methyl-6-oxo-2,4-heptadienal are less than 1% of the mass of 2-methyl-6-oxo-2,4-heptadienal in said composition.

11. The pharmaceutical composition of claim 10, further comprising an anticancer agent selected from mechiorethamine, cyclophosphamide, ifosfamide, melphalan, chlorambucil, uracil mustard, estramustine, mitomycin C, AZQ, thiotepa, busulfan, hepsulfam, carmustine, lomustine, semustine, streptozocin, dacarbazine, cisplatin, carboplatin, procarbazine, methotrexate, trimetrexate, fluouracil, floxuridine, cytarabine, fludarabine phosphate, azacitidine, thioguanine, mercaptopurine, cladribine, allopurine, gemcitabine, pentostatin, vinblastine, vincristine, etoposide, teniposide, topotecan, irinotecan, camptothecin, 9-aminocamptothecin, paclitaxel, docetaxel, daunorubicin, doxorubicin, dactinomycin, idarubincin, plicamycin, mitomycin, amsacrine, bleomycin, aminoglutethimide, anastrozole, finasteride, ketoconazole, tamoxifen, flutamide, leuprolide, goserelin, imatinib mesylate, Leflunomide, SU5416, SU6668, PTK787, gefitinib, erlotinib hydrochloride, trastuzumab, cetuximab, PKI166, GW2016, EKB-509, EKB-569, MDX-H210, 2C4, MDX-447, ABX-EGF, CI-1033, bevacizumab, IMC-1C11, ZD4190, ZD6474, CEP-701, CEP-751, MLN518, PKC412, 13-cis-retinoic acid, isotretinoin, retinyl palmitate, 4-(hydroxycarbophenyl) retinamide, misonidazole, nitracrine, mitotoxantrone, hydroxyurea, 1-asparginase, interferon alfa, rapamycin, CCI-779, and mitotane.

* * * * *

UNITED STATES PATENT AND TRADEMARK OFFICE
CERTIFICATE OF CORRECTION

| | | |
|---|---|---|
| PATENT NO. | : 7,132,458 B2 | Page 1 of 1 |
| APPLICATION NO. | : 10/196695 | |
| DATED | : November 7, 2006 | |
| INVENTOR(S) | : Graham Burton et al. | |

It is certified that error appears in the above-identified patent and that said Letters Patent is hereby corrected as shown below:

On the Title Sheet, in item 56 References Cited, in OTHER PUBLICATIONS,
    In Hardman et al., replace "et al." with --et al.,--;
    In Anon et al., replace "et al." with --et al.,--;
    In Oyler et al., replace "et al. "Characerization " with
    --et al.,"Characterization --;
    In Mordi et al., replace "Raphael C. Mordi, et al." with --Raphael C. Mordi et al.,--.

Column 10, Line 68, within Table 3, Row 1, replace "Cytokeratines" with
    --Cytokeratins--.

Column 11, Line 24, replace "coctail" with --cocktail--.

Column 13,
    Within Table 3, Row 19, replace "immunopositve" with --immunopositive--;
    Within Table 3, Row 21, replace "differention as determined by theintensity"
    with --differentiation as determined by the intensity--;
    Line 34, replace "neuorofilament" with --neurofilament--.

Column 14,
    Line 52, replace "Anitcancer" with --Anticancer--;
    Line 53, replace "anticaner" with --anticancer--.

Column 20, Within Table 13, Row 9, replace "myeloma,neuroblastoma" with
    --myeloma, neuroblastoma--.

Signed and Sealed this

Twenty-seventh Day of March, 2007

JON W. DUDAS
*Director of the United States Patent and Trademark Office*